US010058392B2

(12) United States Patent
Lightcap et al.

(10) Patent No.: US 10,058,392 B2
(45) Date of Patent: *Aug. 28, 2018

(54) NEURAL MONITOR-BASED DYNAMIC BOUNDARIES

(71) Applicant: MAKO Surgical Corp., Ft. Lauderdale, FL (US)

(72) Inventors: Chris Alan Lightcap, Davie, FL (US); Hyosig Kang, Weston, FL (US); Arthur E. Quaid, III, Hollywood, FL (US); Rony Abovitz, Draper, UT (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,282

(22) Filed: Oct. 27, 2017

(65) Prior Publication Data

US 2018/0064492 A1 Mar. 8, 2018

Related U.S. Application Data

(60) Continuation of application No. 14/673,521, filed on Mar. 30, 2015, now Pat. No. 9,801,686, which is a (Continued)

(51) Int. Cl.
*G05B 15/00* (2006.01)
*G05B 19/00* (2006.01)
(Continued)

(52) U.S. Cl.
CPC .......... *A61B 34/10* (2016.02); *A61B 5/04001* (2013.01); *A61B 5/0488* (2013.01); (Continued)

(58) Field of Classification Search
CPC ......... A61B 34/10; A61B 34/20; A61B 34/30; A61B 34/37; A61B 34/70; A61B 34/76;
(Continued)

(56) References Cited

U.S. PATENT DOCUMENTS

| 4,747,393 A | 5/1988 | Medwid |
| 4,903,536 A | 2/1990 | Salisbury et al. |

(Continued)

FOREIGN PATENT DOCUMENTS

| AU | 2007254159 | 7/2013 |
| CN | 1684729 | 10/2005 |

(Continued)

OTHER PUBLICATIONS

U.S. Appl. No. 10/357,197, filed Feb. 21, 2006, Quaid et al.
(Continued)

*Primary Examiner* — Rachid Bendidi
(74) *Attorney, Agent, or Firm* — Foley & Lardner LLP

(57) ABSTRACT

A computer-assisted surgery system may have a robotic arm including a surgical tool and a processor communicatively connected to the robotic aim. The processor may be configured to receive, from a neural monitor, a signal indicative of a distance between the surgical tool and a portion of a patient's anatomy including nervous tissue. The processor may be further configured to generate a command for altering a degree to which the robotic aim resists movement based on the signal received from the neural monitor; and send the command to the robotic arm.

7 Claims, 9 Drawing Sheets

Related U.S. Application Data continuation-in-part of application No. 12/144,507, filed on Jun. 23, 2008, which is a division of application No. 11/357,197, filed on Feb. 21, 2006, now Pat. No. 8,010,180, which is a continuation-in-part of application No. 10/384,072, filed on Mar. 6, 2003, now Pat. No. 7,206,626, said application No. 11/357,197 is a continuation-in-part of application No. 10/384,194, filed on Mar. 6, 2003, now Pat. No. 7,747,311, said application No. 11/357,197 is a continuation-in-part of application No. 10/384,077, filed on Mar. 6, 2003, now Pat. No. 7,206,627, said application No. 11/357,197 is a continuation-in-part of application No. 10/621,119, filed on Jul. 16, 2003, now Pat. No. 7,831,292, which is a continuation-in-part of application No. 10/384,078, filed on Mar. 6, 2003, now Pat. No. 8,095,200, said application No. 14/673,521 is a continuation-in-part of application No. 13/339,541, filed on Dec. 29, 2011, now Pat. No. 8,996,169.

(60) Provisional application No. 60/655,642, filed on Feb. 22, 2005, provisional application No. 60/759,186, filed on Jan. 17, 2006, provisional application No. 60/362,368, filed on Mar. 6, 2002.

(51) Int. Cl.
| | |
|---|---|
| *A61B 34/10* | (2016.01) |
| *A61B 34/00* | (2016.01) |
| *G06F 3/01* | (2006.01) |
| *A61F 2/30* | (2006.01) |
| *A61B 17/86* | (2006.01) |
| *A61B 17/70* | (2006.01) |
| *A61B 17/17* | (2006.01) |
| *A61B 17/16* | (2006.01) |
| *A61B 5/00* | (2006.01) |
| *A61B 5/0488* | (2006.01) |
| *A61B 5/04* | (2006.01) |
| *A61B 34/30* | (2016.01) |
| *A61F 2/46* | (2006.01) |
| *A61F 2/38* | (2006.01) |
| *A61B 17/00* | (2006.01) |
| *A61B 5/11* | (2006.01) |

(52) U.S. Cl.
CPC ........ *A61B 5/4836* (2013.01); *A61B 17/1671* (2013.01); *A61B 17/1757* (2013.01); *A61B 17/7092* (2013.01); *A61B 17/86* (2013.01); *A61B 34/30* (2016.02); *A61B 34/70* (2016.02); *A61F 2/30942* (2013.01); *G06F 3/016* (2013.01); *A61B 5/1127* (2013.01); *A61B 5/745* (2013.01); *A61B 17/7032* (2013.01); *A61B 34/74* (2016.02); *A61B 2017/0003* (2013.01); *A61B 2017/00119* (2013.01); *A61B 2017/00725* (2013.01); *A61B 2034/107* (2016.02); *A61B 2034/108* (2016.02); *A61B 2034/305* (2016.02); *A61B 2034/306* (2016.02); *A61F 2/38* (2013.01); *A61F 2002/4632* (2013.01); *A61F 2002/4633* (2013.01); *G05B 2219/36432* (2013.01); *G05B 2219/39196* (2013.01); *G05B 2219/40478* (2013.01); *G05B 2219/45117* (2013.01); *G05B 2219/45171* (2013.01); *Y10S 901/08* (2013.01); *Y10S 901/09* (2013.01)

(58) Field of Classification Search
CPC . A61B 90/36; A61B 17/7092; A61B 17/7032; A61B 17/00725; A61B 2018/00339; A61B 2018/0044; A61B 2018/00839; A61B 2034/102; A61B 2034/105; A61B 2034/107; A61B 2034/108; A61B 2034/2048; A61B 2034/2051; A61B 2034/2055; A61B 2034/2059; A61B 2034/2068; A61B 2034/207; A61B 2034/252; A61B 2034/254; A61B 2034/305; A61B 2090/08021; A61B 2090/365; A61B 2090/3983; A61B 34/25; A61B 5/1127; A61B 5/745; A61B 90/14; A61B 90/03; A61B 2/38; B25J 9/1689; G06F 3/016; G05B 2219/36432; G05B 2219/39196; G05B 2219/40478; G05B 2219/45117; G05B 2219/45171; Y10S 901/02; Y10S 901/34; Y10S 901/35

See application file for complete search history.

(56) References Cited

U.S. PATENT DOCUMENTS

| | | |
|---|---|---|
| 4,979,949 A | 12/1990 | Matsen et al. |
| 5,046,375 A | 9/1991 | Salisbury et al. |
| 5,086,401 A | 2/1992 | Glassman et al. |
| 5,142,930 A | 9/1992 | Allen et al. |
| 5,154,717 A | 10/1992 | Matsen et al. |
| 5,207,114 A | 5/1993 | Salisbury et al. |
| 5,230,338 A | 7/1993 | Allen et al. |
| 5,236,432 A | 8/1993 | Matsen et al. |
| 5,299,288 A | 3/1994 | Glassman et al. |
| 5,343,385 A | 8/1994 | Joskowicz et al. |
| 5,388,480 A | 2/1995 | Townsend |
| 5,399,951 A | 3/1995 | Lavallee et al. |
| 5,402,801 A | 4/1995 | Taylor |
| 5,408,409 A | 4/1995 | Glassman et al. |
| 5,445,144 A | 8/1995 | Wodicka et al. |
| 5,445,166 A | 8/1995 | Taylor |
| 5,452,941 A | 9/1995 | Halse et al. |
| 5,551,429 A | 9/1996 | Fitzpatrick et al. |
| 5,572,999 A | 11/1996 | Funda et al. |
| 5,576,727 A | 11/1996 | Rosenberg et al. |
| 5,587,937 A | 12/1996 | Massie et al. |
| 5,611,353 A | 3/1997 | Dance et al. |
| 5,625,576 A | 4/1997 | Massie et al. |
| 5,630,431 A | 5/1997 | Taylor |
| 5,638,819 A | 6/1997 | Manwaring et al. |
| 5,676,673 A | 10/1997 | Ferre et al. |
| 5,682,886 A | 11/1997 | Delp et al. |
| 5,688,280 A | 11/1997 | Booth et al. |
| 5,694,013 A | 12/1997 | Stewart et al. |
| 5,695,500 A | 12/1997 | Taylor et al. |
| 5,701,140 A | 12/1997 | Rosenberg et al. |
| 5,704,791 A | 1/1998 | Gillio |
| 5,727,554 A | 3/1998 | Kalend et al. |
| 5,766,016 A | 6/1998 | Sinclair et al. |
| 5,769,640 A | 6/1998 | Jacobus et al. |
| 5,792,147 A | 8/1998 | Evans et al. |
| 5,799,055 A | 8/1998 | Peshkin et al. |
| 5,806,518 A | 9/1998 | Mittelstadt |
| 5,831,408 A | 11/1998 | Jacobus et al. |
| 5,855,553 A | 1/1999 | Tajima et al. |
| 5,871,018 A | 2/1999 | Delp et al. |
| 5,887,121 A | 3/1999 | Funda et al. |
| 5,888,220 A | 3/1999 | Felt et al. |
| 5,898,599 A | 4/1999 | Massie et al. |
| 5,928,137 A | 7/1999 | Green |
| 5,950,629 A | 9/1999 | Taylor et al. |
| 5,971,997 A | 10/1999 | Guthrie et al. |
| 5,976,156 A | 11/1999 | Taylor et al. |
| 5,978,696 A | 11/1999 | Vomlehn et al. |
| 5,980,535 A | 11/1999 | Barnett et al. |
| 5,984,930 A | 11/1999 | MacIunas et al. |
| 5,987,960 A | 11/1999 | Messner et al. |
| 6,002,859 A | 12/1999 | Digioia, III et al. |

(56) References Cited

U.S. PATENT DOCUMENTS

| | | |
|---|---|---|
| 6,006,126 A | 12/1999 | Cosman |
| 6,006,127 A | 12/1999 | Van Der Brug et al. |
| 6,017,305 A | 1/2000 | Bonutti |
| 6,033,415 A | 3/2000 | Mittelstadt et al. |
| 6,084,587 A | 7/2000 | Tarr et al. |
| 6,104,158 A | 8/2000 | Jacobus et al. |
| 6,109,270 A | 8/2000 | Mah et al. |
| 6,111,577 A | 8/2000 | Zilles et al. |
| 6,113,395 A | 9/2000 | Hon |
| 6,147,674 A | 11/2000 | Rosenberg et al. |
| 6,161,032 A | 12/2000 | Acker |
| 6,188,728 B1 | 2/2001 | Hurst |
| 6,191,796 B1 | 2/2001 | Tarr |
| 6,205,411 B1 | 3/2001 | Digioia, III et al. |
| 6,219,032 B1 | 4/2001 | Rosenberg et al. |
| 6,223,100 B1 | 4/2001 | Green |
| 6,226,566 B1 | 5/2001 | Funda et al. |
| 6,228,089 B1 | 5/2001 | Wahrburg |
| 6,231,526 B1 | 5/2001 | Taylor et al. |
| 6,233,504 B1 | 5/2001 | Das et al. |
| 6,259,806 B1 | 7/2001 | Green |
| 6,285,902 B1 | 9/2001 | Kienzle et al. |
| 6,288,705 B1 | 9/2001 | Rosenberg et al. |
| 6,292,174 B1 | 9/2001 | Mallett et al. |
| 6,300,936 B1 | 10/2001 | Braun et al. |
| 6,322,467 B1 | 11/2001 | Hook et al. |
| 6,322,567 B1 | 11/2001 | Mittelstadt et al. |
| 6,325,808 B1 | 12/2001 | Bernard et al. |
| 6,337,994 B1 | 1/2002 | Stoianovici et al. |
| 6,366,273 B1 | 4/2002 | Rosenberg et al. |
| 6,369,834 B1 | 4/2002 | Zilles et al. |
| 6,377,011 B1 | 4/2002 | Ben-Ur |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,393,340 B2 | 5/2002 | Funda et al. |
| 6,405,072 B1 | 6/2002 | Cosman |
| 6,405,158 B1 | 6/2002 | Massie et al. |
| 6,417,638 B1 | 7/2002 | Guy et al. |
| 6,421,048 B1 | 7/2002 | Shih et al. |
| 6,424,885 B1 | 7/2002 | Niemeyer et al. |
| 6,430,434 B1 | 8/2002 | Mittelstadt |
| 6,434,416 B1 | 8/2002 | Mizoguchi et al. |
| 6,443,894 B1 | 9/2002 | Sumanaweera et al. |
| 6,466,815 B1 | 10/2002 | Saito et al. |
| 6,468,265 B1 | 10/2002 | Evans et al. |
| 6,493,608 B1 | 12/2002 | Niemeyer |
| 6,494,039 B2 | 12/2002 | Pratt et al. |
| 6,499,488 B1 | 12/2002 | Hunter et al. |
| 6,533,737 B1 | 3/2003 | Brosseau et al. |
| 6,546,277 B1 | 4/2003 | Franck et al. |
| 6,547,782 B1 | 4/2003 | Taylor |
| 6,551,325 B2 | 4/2003 | Neubauer et al. |
| 6,552,722 B1 | 4/2003 | Shih et al. |
| 6,583,161 B1 | 6/2003 | Medina |
| 6,642,686 B1 | 11/2003 | Ruch |
| 6,665,554 B1 | 12/2003 | Charles et al. |
| 6,671,651 B2 | 12/2003 | Goodwin et al. |
| 6,674,916 B1 | 1/2004 | Deman et al. |
| 6,676,669 B2 | 1/2004 | Charles et al. |
| 6,690,964 B2 | 2/2004 | Bieger et al. |
| 6,692,485 B1 | 2/2004 | Brock et al. |
| 6,701,174 B1 | 3/2004 | Krause et al. |
| 6,702,821 B2 | 3/2004 | Bonutti |
| 6,704,694 B1 | 3/2004 | Basdogan et al. |
| 6,711,431 B2 | 3/2004 | Sarin et al. |
| 6,711,432 B1 | 3/2004 | Krause et al. |
| 6,748,819 B2 | 6/2004 | Maeguchi et al. |
| 6,750,877 B2 | 6/2004 | Rosenberg et al. |
| 6,757,582 B2 | 6/2004 | Brisson et al. |
| 6,770,078 B2 | 8/2004 | Bonutti |
| 6,778,850 B1 | 8/2004 | Adler et al. |
| 6,785,572 B2 | 8/2004 | Yanof et al. |
| 6,786,896 B1 | 9/2004 | Madhani et al. |
| 6,801,801 B1 | 10/2004 | Sati |
| 6,810,281 B2 | 10/2004 | Brock et al. |
| 6,816,148 B2 | 11/2004 | Mallett et al. |
| 6,831,640 B2 | 12/2004 | Shih et al. |
| 6,850,794 B2 | 2/2005 | Shahidi |
| 6,853,965 B2 | 2/2005 | Massie et al. |
| 6,859,661 B2 | 2/2005 | Tuke |
| 6,877,239 B2 | 4/2005 | Leitner et al. |
| 6,894,678 B2 | 5/2005 | Rosenberg et al. |
| 6,920,347 B2 | 7/2005 | Simon et al. |
| 6,985,133 B1 | 1/2006 | Rodomista et al. |
| 6,987,504 B2 | 1/2006 | Rosenberg et al. |
| 7,001,346 B2 | 2/2006 | White |
| 7,035,716 B2 | 4/2006 | Harris et al. |
| 7,039,866 B1 | 5/2006 | Rosenberg et al. |
| 7,104,996 B2 | 9/2006 | Bonutti |
| 7,131,073 B2 | 10/2006 | Rosenberg et al. |
| 7,168,042 B2 | 1/2007 | Braun et al. |
| 7,199,790 B2 | 4/2007 | Rosenberg et al. |
| 7,206,626 B2 | 4/2007 | Quaid, III |
| 7,206,627 B2 | 4/2007 | Abovitz et al. |
| 7,225,115 B2 | 5/2007 | Jones |
| 7,491,198 B2 | 2/2009 | Kockro |
| 7,605,800 B2 | 10/2009 | Rosenberg |
| 7,660,623 B2 | 2/2010 | Hunter et al. |
| 7,683,565 B2 | 3/2010 | Quaid et al. |
| 7,717,932 B2 * | 5/2010 | McFarlin ............ A61B 17/1622 606/170 |
| 7,742,804 B2 | 6/2010 | Faul |
| 7,747,311 B2 | 6/2010 | Quaid, III |
| 7,774,044 B2 | 8/2010 | Sauer et al. |
| 7,831,292 B2 | 11/2010 | Quaid et al. |
| 7,947,050 B2 | 5/2011 | Lee et al. |
| 7,947,051 B2 | 5/2011 | Lee et al. |
| 7,974,677 B2 | 7/2011 | Mire et al. |
| 7,996,110 B2 | 8/2011 | Lipow et al. |
| 8,005,571 B2 | 8/2011 | Sutherland et al. |
| 8,010,180 B2 | 8/2011 | Quaid et al. |
| 8,109,942 B2 | 2/2012 | Carson |
| 8,287,522 B2 | 10/2012 | Moses et al. |
| 8,391,954 B2 | 3/2013 | Quaid, III |
| 8,571,628 B2 | 10/2013 | Kang et al. |
| 8,911,499 B2 | 12/2014 | Quaid et al. |
| 9,002,426 B2 | 4/2015 | Quaid et al. |
| 9,492,237 B2 | 11/2016 | Kang et al. |
| 2001/0002830 A1 | 6/2001 | Rahn et al. |
| 2001/0005815 A1 | 6/2001 | Rosenberg et al. |
| 2001/0034530 A1 | 10/2001 | Malackowski et al. |
| 2001/0036245 A1 | 11/2001 | Kienzle et al. |
| 2001/0037064 A1 | 11/2001 | Shahidi |
| 2001/0039422 A1 | 11/2001 | Carol et al. |
| 2001/0041838 A1 | 11/2001 | Holupka et al. |
| 2002/0038085 A1 | 3/2002 | Immerz |
| 2002/0062177 A1 | 5/2002 | Hannaford et al. |
| 2002/0082498 A1 | 6/2002 | Wendt et al. |
| 2002/0107521 A1 | 8/2002 | Petersen et al. |
| 2002/0108054 A1 | 8/2002 | Moore et al. |
| 2003/0093103 A1 | 5/2003 | Malackowski et al. |
| 2003/0112281 A1 | 6/2003 | Sriram et al. |
| 2003/0128187 A1 | 7/2003 | Strubbe |
| 2003/0187351 A1 | 10/2003 | Franck et al. |
| 2003/0208122 A1 | 11/2003 | Melkent et al. |
| 2003/0208296 A1 | 11/2003 | Brisson et al. |
| 2003/0209096 A1 | 11/2003 | Pandey et al. |
| 2004/0009459 A1 | 1/2004 | Anderson et al. |
| 2004/0012806 A1 | 1/2004 | Murata |
| 2004/0034282 A1 | 2/2004 | Quaid et al. |
| 2004/0102866 A1 | 5/2004 | Harris et al. |
| 2004/0115606 A1 | 6/2004 | Davies |
| 2004/0127788 A1 | 7/2004 | Arata |
| 2004/0128026 A1 * | 7/2004 | Harris ................... B25J 9/1689 700/245 |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0013477 A1 | 1/2005 | Ratti et al. |
| 2005/0027397 A1 | 2/2005 | Niemeyer |
| 2005/0062738 A1 | 3/2005 | Handley et al. |

(56) References Cited

U.S. PATENT DOCUMENTS

| | | |
|---|---|---|
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0137599 A1 | 6/2005 | Masini |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0203536 A1 | 9/2005 | Laffargue et al. |
| 2005/0203539 A1 | 9/2005 | Grimm et al. |
| 2005/0215879 A1 | 9/2005 | Chuanggui |
| 2005/0215888 A1 | 9/2005 | Grimm et al. |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0098851 A1 | 5/2006 | Shoham et al. |
| 2006/0109266 A1 | 5/2006 | Itkowitz et al. |
| 2006/0133827 A1 | 6/2006 | Becouarn et al. |
| 2006/0142657 A1* | 6/2006 | Quaid ............... A61B 17/1764 600/424 |
| 2006/0265179 A1 | 11/2006 | Jansen et al. |
| 2006/0293598 A1 | 12/2006 | Fraser |
| 2007/0142751 A1 | 6/2007 | Kang et al. |
| 2007/0260140 A1 | 11/2007 | Solar et al. |
| 2007/0270685 A1 | 11/2007 | Kang et al. |
| 2008/0004632 A1 | 1/2008 | Sutherland et al. |
| 2008/0004633 A1 | 1/2008 | Arata et al. |
| 2008/0010705 A1* | 1/2008 | Quaid ............... A61B 17/1764 600/407 |
| 2008/0058945 A1 | 3/2008 | Hajaj et al. |
| 2009/0000626 A1 | 1/2009 | Quaid et al. |
| 2009/0012532 A1 | 1/2009 | Quaid et al. |
| 2009/0306499 A1 | 12/2009 | Van Vorhis et al. |
| 2010/0170362 A1* | 7/2010 | Bennett ............ A61B 17/32002 74/490.04 |
| 2010/0198219 A1* | 8/2010 | McFarlin ........... A61B 17/1622 606/45 |
| 2011/0082462 A1 | 4/2011 | Suarez et al. |
| 2011/0082468 A1 | 4/2011 | Hagag et al. |
| 2011/0082587 A1 | 4/2011 | Ziaei et al. |
| 2011/0213383 A1 | 9/2011 | Lee et al. |
| 2011/0270120 A1* | 11/2011 | McFarlin ............ A61N 1/36 600/554 |
| 2012/0109152 A1 | 5/2012 | Quaid, III |
| 2012/0176306 A1* | 7/2012 | Lightcap ............ G06F 3/016 345/156 |
| 2013/0053648 A1 | 2/2013 | Abovitz et al. |
| 2013/0096573 A1* | 4/2013 | Kang ............. A61B 34/30 606/130 |
| 2013/0096574 A1* | 4/2013 | Kang ............. A61B 17/1622 606/130 |
| 2014/0350571 A1* | 11/2014 | Maillet ............. B25J 19/026 606/130 |

FOREIGN PATENT DOCUMENTS

| | | |
|---|---|---|
| EP | 1 059 067 A1 | 12/2000 |
| EP | 1 184 684 A2 | 3/2002 |
| EP | 1 380 266 A1 | 1/2004 |
| EP | 1 871 267 | 1/2008 |
| EP | 1 574 186 | 6/2008 |
| JP | 08-215211 A | 8/1996 |
| JP | 09-330016 A | 12/1997 |
| JP | 2000-279425 A | 10/2000 |
| JP | 2002-102251 | 4/2002 |
| JP | 2003-053684 | 2/2003 |
| JP | 2004-513684 | 5/2004 |
| WO | WO-95/01757 A1 | 1/1995 |
| WO | WO-96/17552 A1 | 6/1996 |
| WO | WO-00/35336 a2 | 6/2000 |
| WO | WO-02/00131 A1 | 1/2002 |
| WO | WO-02/24051 A2 | 3/2002 |
| WO | WO-02/060653 A2 | 8/2002 |
| WO | WO-02/061371 A1 | 8/2002 |
| WO | WO-02/061688 | 8/2002 |
| WO | WO-03/077101 A2 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO-2004/070577 A2 | 8/2004 |
| WO | WO-2004/070580 A2 | 8/2004 |
| WO | WO-2004/070581 A2 | 8/2004 |
| WO | WO-2004/075987 A1 | 9/2004 |
| WO | WO-2005/009215 A2 | 2/2005 |
| WO | WO-2005/072629 A1 | 8/2005 |
| WO | WO-2005/091220 A1 | 9/2005 |
| WO | WO-2005/120380 A1 | 12/2005 |
| WO | WO-2005/122916 A1 | 12/2005 |
| WO | WO-2006/004894 A2 | 1/2006 |
| WO | WO-2006/091494 A1 | 8/2006 |
| WO | WO-2007/117297 A2 | 10/2007 |

OTHER PUBLICATIONS

U.S. Appl. No. 10/384,072, filed Mar. 6, 2003, Quaid, III.

U.S. Appl. No. 11/646,204.

Abovitz et al., "The Future Use of Networked Haptic Learning Information Systems in Computer-Assisted Surgery," CAOS 2001, Jul. 6-8, 2001, pp. 337-338.

Abovitz, "Digital surgery: the future of medicine and human-robot symbiotic interaction," Industrial Robot: An International Journal, Oct. 2001, vol. 28, Issue 5, pp. 401-406 (abstract only).

Abovitz, "Human-Interactive Medical Robotics," CAOS 2000, Jun. 15-17, 2000, pp. 71-72.

Abovitz, "Human-Interactive Medical Robotics," CAOS 2001, Jul. 6-8, 2001, pp. 81-82.

Acosta, et al., "Development of a Haptic Virtual Environment", Computer-Based Medical Systems, Proceedings 12th IEEE Symposium. pp. 35-39, 1999.

Bainville, et al., Concepts and Methods of Registration for Computer-Integrated Surgery, Computer Assisted Orthopedic Surgery (CAOS), 1999, Hogrefe & Huber Publishers, 22 pages.

Bennett et al., "Autonomous Calibration of Single-Loop Kinematic Chains Formed by Manipulators With Passive End-Point Constraints," IEEE Transactions on Robotics and Automation, vol. 7, pp. 597-606, 1991.

Bettini et al., "Vision assisted control for manipulation using virtual fixtures: Experiments at macro and micro scales," in Proc. 2002 IEEE Intl. Conf. on Robotics and Automation, (Washington, DC), May 2002, 8 pages.

Burghart, et al., Robot Controlled Osteotomy in Craniofacial Surgery, 1st International Workshop on Haptic Devices in Medical Applications Proceedings, Institute for Process Control and Robotics, Jun. 23, 1999, 13 pages.

Chapter II Demand and Response to Written Opinion for PCT/US2006/005700, submitted Dec. 15, 2006, 16 pages.

Chapter II Demand and Response to Written Opinion for PCT/US2006/049216, submitted Jul. 15, 2008, 19 pages.

Chen et al., "Force Feedback for Surgical Simulation," Proceedings of the IEEE, New York, US, vol. 86, No. 3, Mar. 1, 1998. pp. 524-530.

Cobb et al., "A robotic system for TKR surgery," in Third Annual North American Program on Computer Assisted Orthopaedic Surgery, (Pittsburgh, PA), pp. 70-74, Jun. 1999.

Colgate, J. Edward, et al., "Cobots: Robots for Collaboration with Human Operators," proceedings of International Mechanical Engineering Congress & Exhibition, DSC-vol. 58, 1996, pp. 433-439.

Communication Pursuant to Article 94(3) EPC for EP Application No. 06735388.8, dated Apr. 6, 2016, 5 pages.

Davies et al, "Acrobot-using Robots and Surgeons Synergistically in Knee Surgery", 1997 British Crown Copyright, pp. 173-178.

Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.

(56) References Cited

OTHER PUBLICATIONS

Davies, B., Computer-assisted and robotics surgery, International Congress and Symposium Series No. 223, 1997, Royal Society of Medicine Press Limited, 12 pages.
Decision to Refuse a European Patent Application for EP Application No. 07756266.8 dated Aug. 3, 2016, 32 pages.
Examination report for EP 04757075.9, dated Jan. 12, 2011, 5 pages.
Fritz, et al., "Design of a Haptic Data Visualization System for People with Visual Impairments", IEEE Trans. on Rehabilitation Engineering, vol. 7, No. 3, Sep. 1999, 13 pages.
Germano et al., Clinical Use of the Optical Digitizer for Intracranial Neuronavigation, Neurosurgery, vol. 45(2), Aug. 1999, 15 pages.
Goswami, et al., "Identifying Robot Parameters Using Partial Pose Information," IEEE Control Systems Magazine, vol. 13, No. 5, Oct. 1993, 11 pages.
Harris, et al., Experiences with Robotic Systems for Knee Surgery, CVR Med-MRCAS'97 Proceedings of the First Joint Conference on Computer Vision, Virtual Realty, and Robotics in Medicine and Medial Robotics and Computer-Assisted Surgery, Mar. 1997, Springer, 11 pages.
Ho, S.C. et al., "Robot Assisted Knee Surgery Establishing a Force Control Strategy Incorporating Active Motion Constraint," IEEE Engineering in Medicine and Biology Magazine, vol. 14, No. 3, May 1, 1995, col. 2-3, p. 293.
Hollerbach, J.M. & D. E. Johnson. Virtual Environment Rendering. To appear in Human and Machine Haptics, M. Cutkosky, R. Howe, K. Salisbury, and M. Srinivasan (eds.), MIT Press, 2000 (available at http://www.cs.ubc.ca/labs/spin/publications/related/hollerbach00.pdf), 25 pages.
International Preliminary Examination Report for PCT/US2003/007063, dated Sep. 2, 2004 (2 pages).
International Preliminary Report on Patentability for PCT/US2004/022978 including International Search Report and Written Opinion, dated Feb. 13, 2007 (6 pages).
International Preliminary Report on Patentability for PCT/US2006/005700, dated May 8, 2007 (7 pages).
International Preliminary Report on Patentability for PCT/US2006/049216, dated Sep. 10, 2008, 9 pages.
International Search Report and Written Opinion for corresponding PCT Application No. PCT/US2006/049216, dated May 8, 2008 (15 pgs.).
International Search Report and Written Opinion for PCT/US2006/005700, dated Jun. 27, 2006, 10 pages.
International Search Report for PCT/US2003/007063, dated Apr. 16, 2004 (7 pages).
Kanazides, Peter et al., "An Integrated System for Cementless Hip Replacement", Integrated Surgical Systems Department of Orthopedic Surgery, Sutter General Hospital, May/Jun. 1995, pp. 307-313.
Leeser et al., "Computerassisted teach and play: Novel user-friendly robot teach mode using gravity compensation and backdrivability," in Proceedings of the Robotics International/SME Fifth World Conference on Robotics Research, (Cambridge, MA), Sep. 1994, 7 pages.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "'Acrobof'capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Meggiolaro, et al., "Manipulator calibration using a single endpoint contact constraint," in 26th ASME Bienniel Mechanisms Conference, (Baltimore, MD), 2000, 9 pages.
Moore, Carl A., et al., "Cobot Implementation of 3D Virtual Surfaces," proceedings of the 2002 Institute of Electrical and Electronics Engineers International Conference on Robotics & Automation, May 2002, pp. 3242-3247.

Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Park et al., "Virtual fixtures for robotic cardiac surgery," in Proc. Medical Image Computing and Computer-Assisted Intervention, (Utrecht, Netherlands), Oct 2001, 2 pages.
PCT/US2006/049216, Partial Intl. Search Report, Jan. 18, 2008 (2 pgs.).
Press Release, "The Acrobot Company Wins Best Surgical Innovation Award," Acrobot Precision Surgical Systems, May 24, 2002, 1 page.
Provision of a Copy of the Minutes in Accordance with Rule 124(4) EPC for EP Application No. 07756266.8 dated Aug. 2, 2016, 5 pages.
Quaid et al., "Haptic Information Displays for Computer-Assisted Surgery," Proceedings of the 2002 IEEE International Conference on Robotics & Automation, May 2002, pp. 2092-2097.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.
Roche, "Changing the way surgeons plan and execute minimally invasive unicompartmental knee surgery," Orthopaedic Product News, pp. 16-18, Jul./Aug. 2006.
Rosenberg, "Virtual Fixtures: Perceptual Tools for Telerobotic Manipulation", 1993 IEEE, 76-82.
Rosenberg, Virtual Fixtures: Perceptual overlays enhance operator performance in telepresence tasks. PhD thesis, Stanford University, Aug. 1994, 7 pages.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider, O., et al., "Synergistic Robotic Assistance to Cardiac Procedures," presented to Computer Assisted Radiology and Surgery on Jun. 23-26, 1999, 5 pages.
Sensable Technologies, Inc., "Freeform Feel the Difference", 2001, 4 pages.
Sensable Technologies, Inc., "FreeForm Modeling—Technical Features," 2003, 2 pages.
Staecker et al., "Use of the LandmarX (tm) Surgical Navigation System in Lateral Skull Base and Temporal Bone Surgery", SkullBase, vol. 11, No. 4, 2001, pp. 245-255; Thieme Medical Publishers, Inc. 11 pages.
Steines et al., Segmentation of Osteoarthritic Femoral Cartilage Using Live Wire, Proc. Intl. Soc. Mag. Reson. Med. 8, 2000, 1 page.
Taylor, Russell et al., "An Image-Directed Robotic System for Precise Orthopaedic Surgery", IEEE Transactions on Robotics and Automation, vol. 10, No. 3, Jun. 1994, pp. 261-275.
Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.
Taylor, Russell et al., "Robotic Joint Replacement Surgery", NSF Engineering Research Center for Computer-Integrated Surgical Systems and Technology, 2000, 2001, 2004, 71 pages.
Tognetti, Lawrence Joseph, "Actuator Design for a Passive Haptic Display," Georgia Institute of Technology, Jun. 1999, 33 pages.
Townsend et al., "Teleoperator slave—WAM design methodology," Industrial Robot, vol. 26, No. 3, pp. 167-177, 1999.
World Wide Web, http://haptics.me.jhu.edu/r.sub.--hapt.html, "Haptic Interfaces and Virtual Environments," printed on Jun. 12, 2003, 2 pages.
World Wide Web, http://haptics.me.jhu.edu/r.sub.--kine.html, "Robot Design and Kinematics," printed on Jun. 12, 2003, 2 pages.

(56) References Cited

OTHER PUBLICATIONS

World Wide Web, http://www.acrobot.co.uk/background.html, "The Acrobot Company Limited—Background," printed on Jul. 10, 2002, 1 page.
World Wide Web, http://www.acrobot.co.uk/home.html, "The Acrobot Company Limited—Precision Surgical Systems," printed on Jul. 10, 2002, 1 page.
World Wide Web, http://www.acrobot.co.uk/meetings.html, "The Acrobot Company Limited—Meetings and Publications," printed on Jul. 10, 2002, pp. 1-3.
World Wide Web, http://www.acrobot.co.uk/products.html, "The Acrobot Company Limited—Products," printed on Jul. 10, 2002, pp. 1-6.
World Wide Web, http://www.fcs-cs.com/robotics/content/assistance.htm, "Surgical Assistance," printed on Jun. 12, 2003, 1 page.
World Wide Web, http://www.fcs-cs.com/robotics/content/design.htm, "Virtual Design, Assembly & Maintenance," printed on Jun. 12, 2003, 1 page.
World Wide Web, http://www.fcs-cs.com/robotics/content/endeffectors.htm, "End effectors," printed on Jun. 12, 2003, 1 page.
World Wide Web, http://www.fcs-cs.com/robotics/content/hapticmaster.htm, "HapticMASTER", printed on Jun. 12, 2003, 1 page.
World Wide Web, http://www.fcs-cs.com/robotics/content/reality.htm, "Virtual Reality," printed on Jun. 12, 2003, 1 page.
World Wide Web, http://www.fcs-cs.com/robotics/content/rehabilitation.htm, "Rehabilitation," printed on Jun. 12, 2003, 1 page.
World Wide Web, http://www.fcs-cs.com/robotics/content/research.htm, "Research," printed on Jun. 12, 2003, 1 page.
World Wide Web, http://www.fcs-cs.com/robotics/content/simulation.htm, "Simulation & Training," printed on Jun. 12, 2003, 1 page.
World Wide Web, http://www.fcs-cs.com/robotics/content/software.htm, "Software," printed on Jun. 12, 2003, 1 page.
World Wide Web, http://www.merl.com/projects/surgSim99/, "Knee Arthroscopy Simulation," printed on Jun. 12, 2003, 2 pages.
Written Opinion for PCT/US2006/049216, dated May 8, 2008, 12 pages.
Zilles, et al., "A Constraint-Based God-object Method for Haptic Display", IEEE Proceedings, pp. 146-151, 1995.

\* cited by examiner

NEURAL MONITOR-BASED DYNAMIC BOUNDARIES

CROSS-REFERENCE TO RELATED APPLICATIONS

This application is a continuation of U.S. application Ser. No. 14/673,521, filed Mar. 30, 2015, which is continuation-in-part of U.S. application Ser. No. 13/339,541, filed Dec. 29, 2011, U.S. application Ser. No. 14/673,521, filed Mar. 30, 2015, is also a continuation-in-part of U.S. application Ser. No. 12/144,507, filed Jun. 23, 2008, which is a divisional of U.S. application Ser. No. 11/357,197, filed Feb. 21, 2006, which claims the benefit of and priority to both U.S. Provisional Application No. 60/655,642, filed Feb. 22, 2005 and U.S. Provisional Application No. 60/759,186, filed Jan. 17, 2006.

U.S. application Ser. No. 11/357,197, filed Feb. 21, 2006, is also a continuation-in-part of U.S. application Ser. No. 10/384,072, filed Mar. 6, 2003, which claims the benefit of and priority to U.S. Provisional Application No. 60/362,368, filed Mar. 6, 2002.

U.S. application Ser. No. 11/357,197, filed Feb. 21, 2006, is also a continuation-in-part of U.S. application Ser. No. 10/384,077, filed Mar. 6, 2003, which claims the benefit of and priority to U.S. Provisional Application No. 60/362,368, filed Mar. 6, 2002.

U.S. application Ser. No. 11/357,197, filed Feb. 21, 2006, is also a continuation-in-part of U.S. application Ser. No. 10/384,194, filed Mar. 6, 2003, which claims the benefit of and priority to U.S. Provisional Application No. 60/362,368, filed Mar. 6, 2002.

U.S. application Ser. No. 11/357,197, filed Feb. 21, 2006, is also a continuation-in-part of U.S. application Ser. No. 10/621,119, filed Jul. 16, 2003, which is a continuation-in-part of U.S. application Ser. No. 10/384,078, filed Mar. 6, 2003, which claims the benefit of and priority to U.S. Provisional Application No. 60/362,368, filed Mar. 6, 2002.

The following above-referenced applications are hereby incorporated by reference herein in their entireties: U.S. application Ser. No. 14/673,521 filed Mar. 30, 2015; U.S. application Ser. No. 13/339,541 filed Dec. 29, 2011; U.S. application Ser. No. 10/621,119, filed Jul. 16, 2003; U.S. application Ser. No. 10/384,078, filed Mar. 6, 2003; and U.S. Provisional Application No. 60/362,368, filed Mar. 6, 2002.

TECHNICAL FIELD

The present disclosure relates generally to surgical systems and, more particularly, to dynamically altering the haptic response of a surgical system based on output from a neural monitor.

BACKGROUND

Many surgical procedures depend on accurate drilling or resection of portions of a patient's bone. For example, in various spinal surgeries, a surgeon may be required to drill one or more holes in a patient's spine. However, if the surgeon drills a hole improperly, e.g., too deeply, at an incorrect trajectory or angle, etc., the surgeon may cause irreparable damage to the patient. For instance, a surgeon may be required to drill one or more pilot holes for pedicle screws to be inserted in the patient's spine. If the surgeon drills the pilot holes incorrectly, the surgeon may cause damage to the spinal cord, thereby injuring the patient.

In some surgeries, a surgeon may use a computer-assisted surgery system when drilling or resecting portions of the patient's bone. Moreover, the computer-assisted surgery system may include a haptic feedback system to constrain or inhibit the surgeon from manually moving the surgical tool beyond predefined virtual boundaries defined by haptic objects. The virtual boundaries may be established to prevent the surgeon from undesired interactions with a patient's anatomy. For example, the haptic boundaries may help to prevent the surgeon from improperly drilling or resecting the patient's bone.

However, a variety of factors such as inaccurately or improperly defined haptic boundaries, improper registration of the patient's bone to the computer-assisted surgery system, etc., may affect the accuracy of the computer-assisted surgery system. In some surgeries, such as various spinal surgeries, inaccuracies may lead to undesired interaction with the spinal cord or other nerves and injure the patient. Moreover, in some instances, such interaction may have disastrous consequences, such as full or partial paralysis, nerve damage, etc.

Patient monitoring systems are known that may be used to monitor electromyographic (EMG) activity of a patient to determine the proximity of a cutting tool or other instrument to a patient's nerve. For example, an electrical potential may be applied to the cutting tool, and EMG signals may be read from sensors placed in muscles or other tissue innervated by the nerves of concern. By comparing the electrical signal applied to the cutting tool with the signals from the sensors, the patient monitoring system may determine the distance between the cutting tool and a nerve. Moreover, certain systems may disable power to the cutting tool based on the determined distance.

However, enabling and disabling power to a cutting tool may adversely affect the quality and accuracy of the resection or drilling being performed, especially if the cutting tool continuously toggles between an enabled and disabled state. Moreover, it may be difficult to determine an acceptable threshold distance for disabling power to the cutting tool.

The presently disclosed systems and methods for neural monitor-based dynamic haptics are directed to overcoming one or more of the problems set forth above and/or other problems in the art.

SUMMARY

According to one aspect, the present disclosure is directed to a computer-implemented method for controlling a surgical system. The method may include receiving, from a neural monitor, a signal indicative of a distance between a surgical tool connected to a robotic arm and a portion of a patient's anatomy including nervous tissue. A command may be generated for altering a degree to which the robotic arm resists movement based on the signal received from the neural monitor.

According to another aspect, the present disclosure is directed to a computer-assisted surgery system. The system may include a robotic arm, including a surgical tool, and a processor. The processor may be communicatively connected to the robotic arm and configured to receive, from a neural monitor, a signal indicative of a distance between the surgical tool and a portion of a patient's anatomy including nervous tissue. The processor may be further configured to generate a command for altering a degree to which the robotic arm resists movement based on the signal received from the neural monitor; and send the command to the robotic arm.

According to yet another aspect, the present disclosure is directed to a computer-implemented method for controlling a surgical system. The method may include receiving, at a processor associated with a computer, a signal from a neural monitor indicative of a distance between a surgical tool connected to a robotic arm and a portion of a patient's anatomy including nervous tissue. The method may also include determining, by the processor, a haptic feedback command based on the signal received from the neural monitor.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

Figure 1:
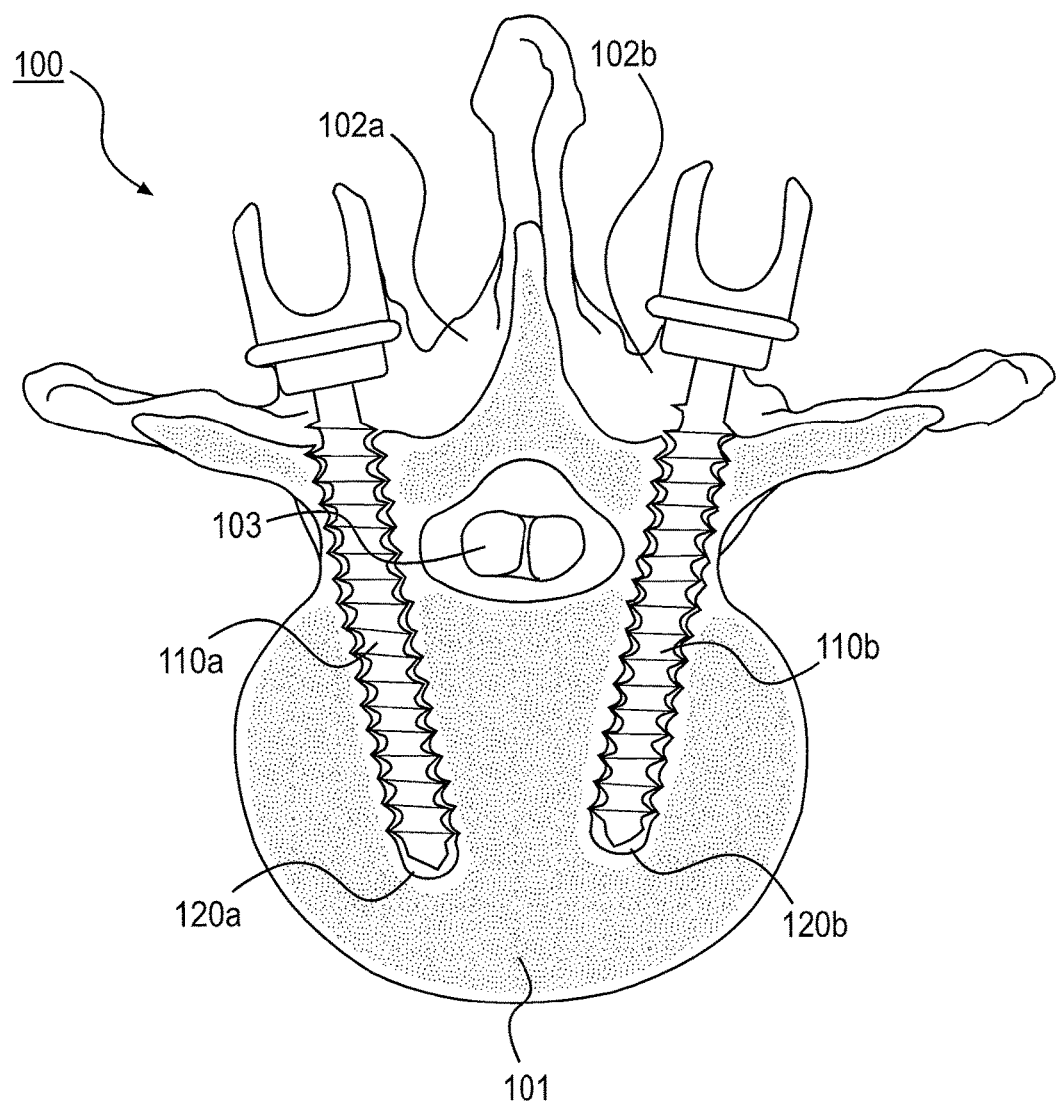
FIG. 1 is an illustration of a surgical environment, consistent with disclosed embodiments.

FIG. 1 illustrates an exemplary surgical environment, consistent with disclosed embodiments. For example, FIG. 1 shows a cross-sectional view of a vertebra 100. During surgery, such as spinal fusion surgery, a surgeon may insert one or more of pedicle screws 110a and 110b through pedicle regions 102a and 102b, respectively, and into vertebral body 101 of vertebra 100. Prior to inserting pedicle screws 110a and 110b, the surgeon may drill or otherwise cut pilot holes 120a and 120b corresponding to pedicle screws 110a and 110b. The pilot holes may facilitate insertion of pedicle screws 110a and 110b into vertebra 100.

As shown in FIG. 1, pedicle screws 110a and 110b may be inserted in close proximity to spinal cord 103, and thus, the placement of pedicle screws 110a and 110b and their corresponding pilot holes must be precisely aligned so as to avoid interacting with or damaging spinal cord 103. If a surgeon drills pilot holes 120a or 120b at an improper angle and/or too deeply, pedicle screws 110a or 110b or the cutting tool used to drill pilot holes 120a and 120b may damage spinal cord 103.

Exemplary embodiments of the present disclosure, discussed in greater detail below, may reduce the risk of injury to spinal cord 103, e.g., by detecting one or more electromyographic (EMG) signals to measure a distance between the cutting tool used to drill pilot holes 120a and 120b and dynamically altering a degree to which a robotic arm connected to the cutting tool resists movement based on the measured distance. This way, if a surgeon operates a cutting tool in dangerous proximity to spinal cord 103, the surgeon may experience haptic feedback from the robotic arm, preventing the surgeon from moving the cutting tool closer to spinal cord 103.

Moreover, as discussed above, FIG. 1 represents an exemplary surgical environment in which embodiments of the present disclosure may be used. For example, disclosed embodiments may be used in spinal surgeries other than spinal fusion, such as dynamic stabilization surgeries, discectomies, foramenotomies, laminectomies, etc. Further, disclosed embodiments may be used in any surgery in which a surgeon may drill, resect, or modify any portion of the patient's anatomy in proximity to spinal cord 103, a nerve or group of nerves, or any other portion of the patient's anatomy including nervous tissue. For example, disclosed embodiments may also be used in surgeries performed in proximity to the facial nerve, such as mastoidectomies or other otolaryngolocial surgeries. EMG signals may be used to measure the distance between a cutting tool and the facial nerve, in accordance with disclosed embodiments.

Figure 2:
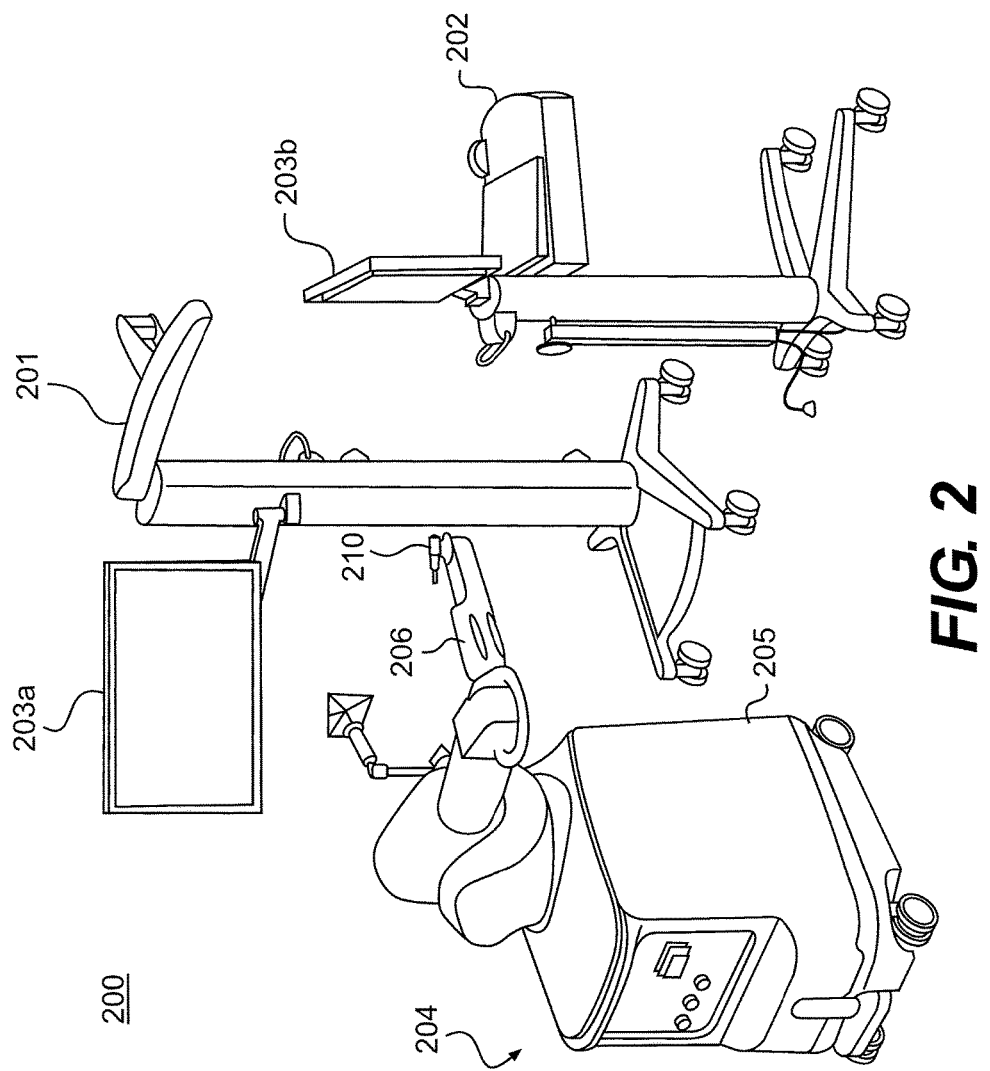
FIG. 2 is an illustration of an exemplary computer-assisted surgery (CAS) system, in which certain methods consistent with the disclosed embodiments may be implemented, consistent with disclosed embodiments.

FIG. 2 illustrates an exemplary computer-assisted surgery (CAS) system 200, in which processes and features associated with certain disclosed embodiments may be implemented. CAS system 200 may be configured to perform a wide variety of surgical procedures, including spinal surgeries such as spinal fusion and dynamic stabilization surgeries, discectomies, foramenotomies, and laminectomies. As illustrated in FIG. 2, CAS system 200 may comprise a tracking system 201, a computer-assisted navigation system 202, one or more display devices 203a, 203b, and a robotic arm 204. It should be appreciated that CAS system 200, as well as the methods and processes described herein, may be applicable to many different types of surgical procedures. Although certain disclosed embodiments may be described with respect to drilling pedicle screw pilot holes for spinal fusion techniques and other operations performed during spinal surgeries, those skilled in the art will appreciate that the concepts and methods described herein may be applicable to other types of surgeries. For example, concepts and methods described herein may be applicable to other procedures where portions of a patient's anatomy may be drilled, resected, or otherwise modified by CAS system 200.

Robotic arm 204 can be used in an interactive manner by a surgeon to perform a surgical procedure, such as a spinal surgery, on a patient. As shown in FIG. 2, robotic aim 204 includes a base 205, an articulated arm 206, a force system (not shown), and a controller (not shown). Articulated arm 206 may include one or more joints about which articulated arm 206 may be pivoted, rotated, or otherwise moved. A surgical tool 210 (e.g., an end effector having an operating member, such as a saw, reamer, burr, drill, etc.) may be coupled to the articulated arm 206. The surgeon can manipulate surgical tool 210 by grasping and manually moving articulated arm 206 and/or surgical tool 210.

The force system and controller are configured to provide control or guidance to the surgeon during manipulation of the surgical tool. The force system is configured to provide at least some force to the surgical tool via articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654, 519 (U.S. Patent Application Pub. No. 2010/0170362), filed Dec. 22, 2009, each of which is hereby incorporated by reference herein in its entirety. According to one embodiment, CAS system 200 is the RIO® Robotic Aim Interactive Orthopedic System manufactured by MAKO Surgical Corp. of Fort Lauderdale, Fla. The force system and controller may be housed within robotic aim 204. Moreover, in certain embodiments, all or part of the force system may be housed within another component of CAS system 200, such as computer-assisted navigation system 202, for example.

Tracking system 201 may include any suitable device or system configured to track the relative locations, positions, orientations, and/or poses of the surgical tool 210 (coupled to robotic arm 204) and/or positions of registered portions of a patient's anatomy, such as bones. Such devices may employ optical, mechanical, or electromagnetic pose tracking technologies. According to one embodiment, tracking system 201 may comprise a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during the surgical procedure, navigation system 202 may display images related to the surgical procedure on one or both of the display devices 203a, 203b.

Figure 3:
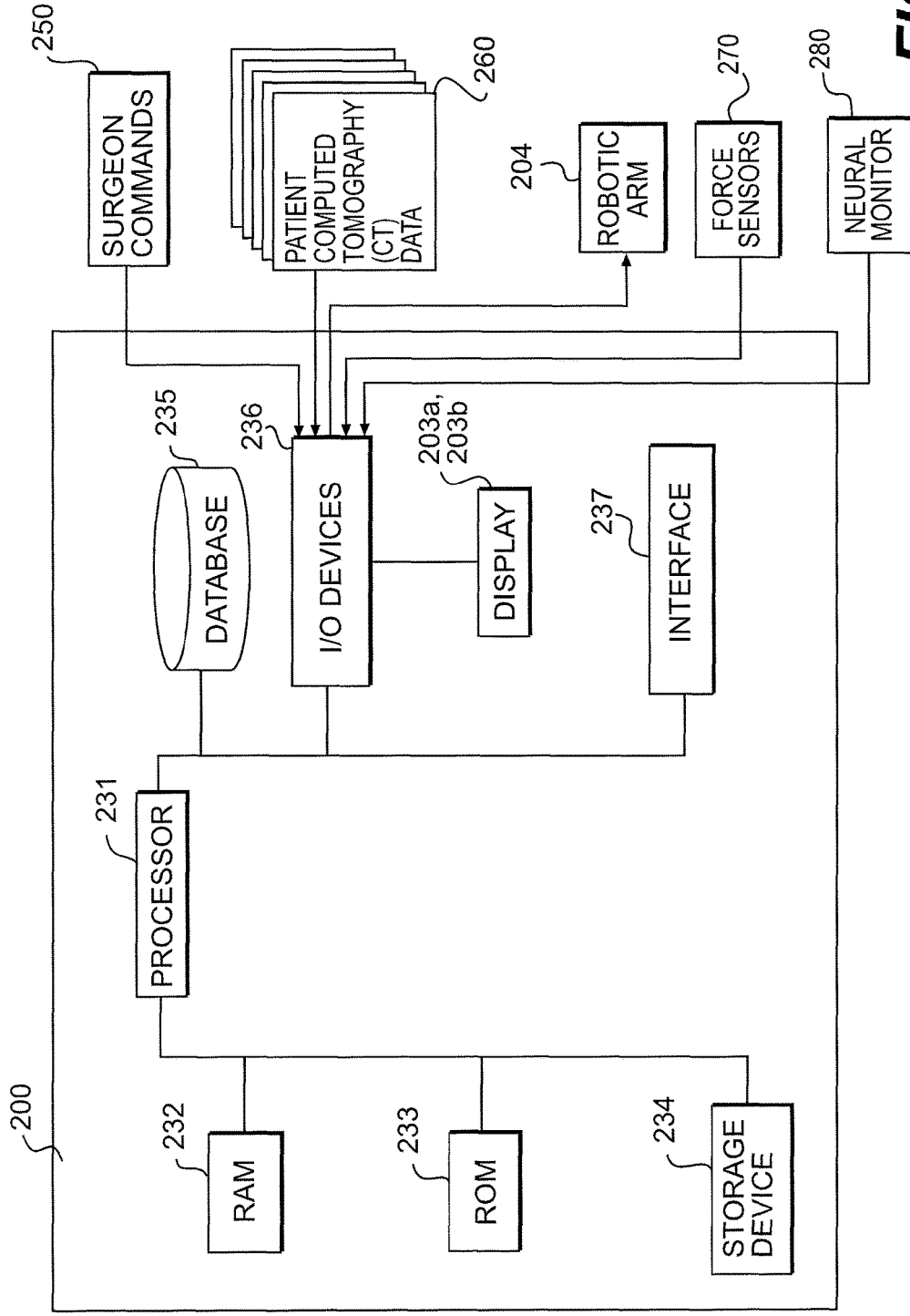
FIG. 3 is a schematic diagram of an exemplary computer system, which may be used in one or more components associated with the CAS system illustrated in FIG. 2.

One or more constituent components of CAS system 200, such as navigation system 202 and/or robotic arm 204, may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as tracking software, surgical navigation software, 3-D bone modeling or imaging software, software for establishing virtual haptic boundaries for use with the force system of robotic arm 204 to provide haptic feedback to surgical tool 210, and/or software for providing dynamic haptic feedback to a surgeon based on a measured distance between surgical tool 210 and a portion of the patient's anatomy, such as spinal cord 103. CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 3, processor 231 may be communicatively coupled to RAM 232, ROM 233, storage device 234, database 235, I/O devices 236, and network interface 237. Processor 231 may be configured to execute sequences of computer program instructions to perform various processes, described in greater detail below. The computer program instructions may be loaded into RAM 232 for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202 and/or robotic arm 204, to perform functions or tasks associated with CAS system 200. For example, computer readable media may include instructions for causing the CAS system 200 to perform one or more methods for dynamically altering a degree to which robotic arm 204 (e.g., articulated aim 206) resists movement based on a distance between surgical tool 210 and a portion of the patient's anatomy, such as spinal cord 103, that may be measured by a neural monitor, for example. In certain embodiments, the instructions may cause CAS system 200 to alter the degree to which robotic arm 204 resists movement by generating a damping torque based on the distance measured by the neural monitor. In other embodiments, the instructions may cause CAS system 200 to alter the degree to which robotic arm 204 resists movement by modifying an amount of force feedback being applied to robotic arm 204 based on the measured distance. In still other embodiments, the instructions may cause CAS system 200 to alter the degree to which robotic arm 204 resists movement by directly modifying a haptic object impedance value or haptic object admittance value based on the measured distance.

Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203a, 203b, including a graphical user interface (GUI) for outputting information on a monitor. I/O devices 236 may also include peripheral devices such as, for example, a printer for printing information associated with CAS system 236, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., bones) in software.

I/O devices 236 may also include one or more components configured to receive information about CAS system 200 and/or information related to a patient undergoing surgery. For example, I/O devices 236 may include one or more force sensors 270. Force sensors 270 may be configured to detect a force being applied to surgical tool 210 and/or articulated arm 206 of robotic arm 204 by the surgeon. Moreover, other sensors (not shown) may also be included that measure, e.g., a position, velocity, and/or acceleration of surgical tool 210 and/or articulated arm 206 and send this information to processor 231. Moreover, I/O devices 236 may include a neural monitor 280 which, as discussed in greater detail below, may generate and send a signal indicative of a distance between surgical tool 210 and a portion of a patient's anatomy including nervous tissue, such as spinal cord 103, for example.

Processor 231 may be configured to establish virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site. During surgery, processor 231 may send haptic feedback commands to robotic arm 204 based on the virtual haptic geometry. For example, processor 231 may determine a distance between surgical tool 210 and one or more virtual representations, and may generate haptic feedback commands based on the distance.

Processor 231 may also generate haptic feedback commands based on a measured distance between surgical tool 210 and a portion of a patient's anatomy, such as spinal cord 103. The distance may be measured, e.g., by neural monitor 280. In certain embodiments, the haptic feedback commands generated based on the distance measured by neural monitor 280 may be combined with the haptic feedback commands generated based on the distance from the virtual representations of the patient's anatomy, such that the haptic feedback command provided to robotic arm 204 is a combination of the two haptic feedback commands.

Figure 4:
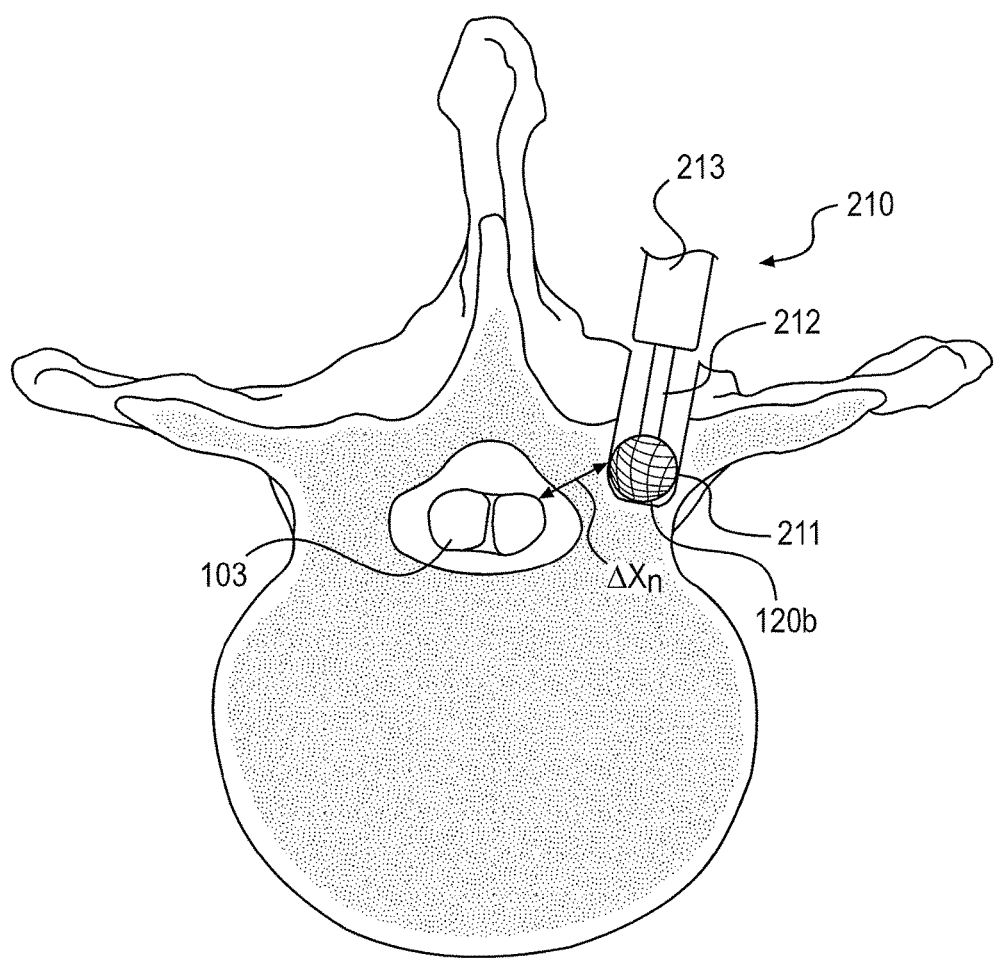
FIG. 4 is another illustration of a surgical environment, consistent with disclosed embodiments.

FIG. 4 is another illustration of a surgical environment, according to exemplary embodiments. In FIG. 4, a surgeon may begin to drill pilot hole 120b with surgical tool 210. At distal end 211, surgical tool 210 may include, e.g., a drill bit, burr, etc., to perform drilling, resection, or any other modification of the patient's anatomy. In exemplary embodiments, an electrical current may be applied to distal end 211. The electrical current may be applied to distal end 211 through shaft 212 via a wire (not shown) electrically connected to shaft 212 through a conductive bearing (not shown) lubricated with conductive grease. The electrical current may be generated, e.g., by neural monitor 280. In other embodiments, the electrical current may be applied to shaft 212 using a conductive brush in contact with shaft 212, similar to a motor commutation system. Moreover, those skilled in the art will appreciate that an electrical current may be applied to distal end 211 via any other means consistent with disclosed embodiments. In certain embodiments, surgical tool 210 may include a non-conductive sleeve 213 to electrically isolate the electrical signal and prevent the user (e.g., a surgeon) from interacting with the signal.

As the surgeon operates surgical tool 210, e.g., to drill pilot hole 120b, the electrical signal applied to distal end 211 may be used by neural monitor 280 to determine a distance, $\Delta x_n$, between distal end 211 and spinal cord 103. For example, in addition to generating the electrical signal, neural monitor 280 may also include one or more sensors or probes located at or around spinal cord 103 and/or in or around muscles innervated by spinal cord 103. Neural monitor 280 may also include a reference sensor or probe in a location separated from spinal cord 103, e.g., on the patient's forehead. Neural monitor 280 may monitor the incoming signals received at these sensors or probes, and may compare the incoming signals to the electrical signal being applied to distal end 211. Based on this comparison, neural monitor 280 may determine a distance between distal end 211 (e.g., the cutting tip of surgical tool 210) and spinal cord 103. While spinal cord 103 is used in the embodiment discussed above, those skilled in the art will appreciate that a distance to any nerve or group of nerves may be determined by neural monitor 280 using similar techniques.

Neural monitor 280 may send signals to CAS system 200 that are indicative of the determined distance between distal end 211 (e.g., the cutting tip of surgical tool 210) and spinal cord 103. CAS system 200 may then dynamically vary the degree to which robotic arm 204 resists movement based on these signals. For example, processor 231 may receive the signals indicating the distance between distal end 211 and spinal cord 103, and, based on these signals, may generate and send one or more commands to robotic arm 204 such that a user operating articulating arm 206 or surgical tool 210 of robotic arm 204 experiences haptic feedback based on the distance between distal end 211 and spinal cord 103, as determined by neural monitor 280. In certain embodiments, the user may experience haptic feedback such that robotic aim 204 becomes more difficult to move as distal end 211 moves closer to spinal cord 103.

FIGS. 5-8, discussed in greater detail below, illustrate exemplary embodiments of how CAS system 200 may dynamically vary the degree to which robotic arm 204 resists movement based on the signals received from neural monitor 280. Those skilled in the art will appreciate that the system control diagrams shown in FIGS. 5-8 may be implemented by processor 231, for example, based on software stored in one or more of RAM 232, ROM 233, and storage device 234.

Figure 5:
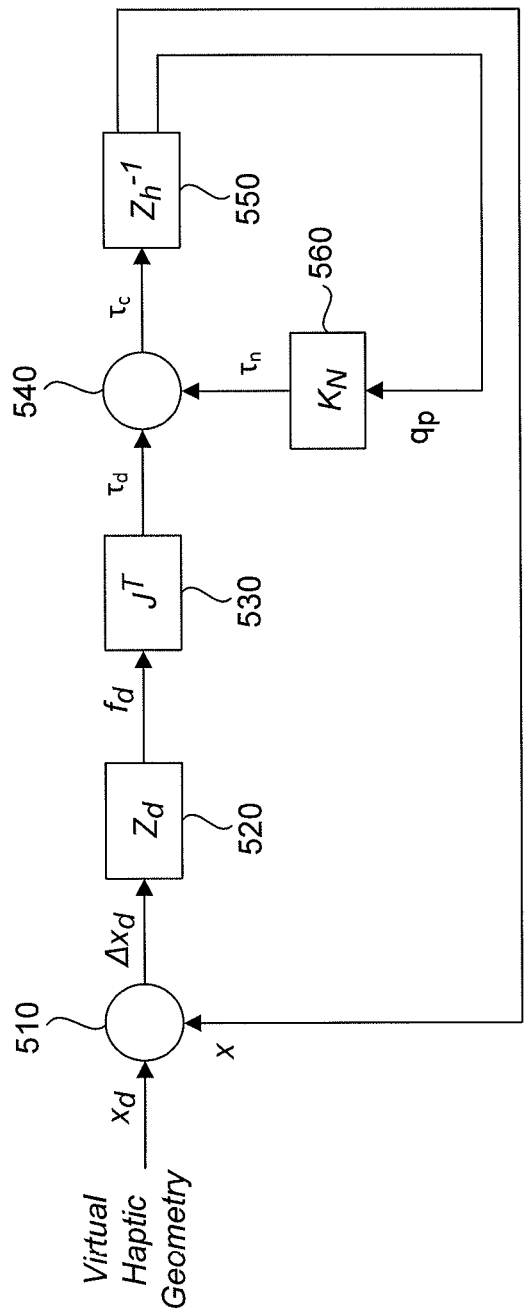
FIG. 5 is a block diagram of an exemplary control system which may be employed by the CAS system illustrated in FIG. 2.

FIG. 5 shows a system control diagram in accordance with an exemplary embodiment in which processor 231 may control robotic arm 204 by means of impedance control. For example, in FIG. 5, processor 231 may alter an impedance of robotic arm 204 based on a virtual damping torque $\tau_n$ generated in accordance with the distance between distal end 211 of surgical tool 210 and spinal cord 103, as measured by neural monitor 280. The virtual damping torque $\tau_n$ may be combined with a torque $\tau_d$ that is generated based on the virtual haptic geometry used to model the patient's anatomy or any other object associated with the surgical environment. This combined torque $\tau_c$ may then be used to generate a haptic feedback command that may be sent to the force system of robotic arm 204. Robotic arm 204 may use the haptic feedback command to control actuators therein so as to vary the impedance of robotic arm 204 based on the command.

For example, in FIG. 5, processor 231 may receive a desired position $x_d$ and an actual position x of surgical tool 210. Desired position $x_d$ and actual position x may include a point or set of points in three-dimensional space to represent their respective positions. Desired position $x_d$ may be determined based on the virtual haptic geometry used to model the patient's anatomy and/or objects associated with the surgical environment. For example, desired position $x_d$ may be a point or set of points located at the edge of a virtual boundary created based on one or more of the haptic objects. The actual position x of surgical tool 210 may be detected by tracking system 201 or by one or more position sensors configured to measure angular positions of one or more joints in robotic arm 204, for example.

Processor 231 may calculate a difference $\Delta x_d$ between the desired position and the actual position of surgical tool 210 (block 510). Processor 231 may then calculate a haptic object force $f_d$ based on difference $\Delta x_d$ (block 520). For example, processor 231 may calculate $f_d$ by multiplying difference $\Delta x_d$ by a haptic object impedance value $Z_d$. In certain embodiments, haptic object impedance value $Z_d$ may be a fixed value for the haptic object to which it corresponds, e.g., haptic object impedance value $Z_d$ may be 3,000 N/m for a particular haptic object. In other embodiments, discussed in greater detail below, haptic object impedance value $Z_d$ may be variable.

In certain embodiments, haptic object impedance value $Z_d$ may include an inertia component M, a damping component B, and a stiffness component K. In this embodiment, processor 231 may also determine a first derivative and/or a second derivative of the difference values $\Delta x_d$, and may calculate haptic object force $f_d$ based on the impedance components M, B, and/or K as well as $\Delta x_d$ and its first and/or second derivatives. For example, processor 231 may determine $f_d$ in accordance with the following equation:

$$f_d = M(\Delta \ddot{x}_d) + B(\Delta \dot{x}_d) + K(\Delta x_d), \quad (1)$$

where M, B, and K are each constant values. In one embodiment, M may be equal to zero, such that $f_d$ is determined based on a damping component B and a stiffness component K. Of course, in other embodiments, any combination of M, B, and K may be zero, such that $f_d$ is determined based on the remaining non-zero components.

After calculating haptic object force $f_d$, processor 231 may calculate a haptic object torque $\tau_d$ to be applied to robotic arm 204, e.g. by one or more actuators at corresponding joints of robotic arm 204 (block 530). Thus, at block 530, processor 231 may utilize the Jacobian transpose to determine a haptic object torque $\tau_d$ that will generate a force at articulated arm 206 equal to haptic object force $f_d$.

In certain embodiments, neural monitor torque $\tau_n$ may embody a virtual damping torque. For example, processor 231 may calculate neural monitor torque $\tau_n$ at block 560 as $\tau_n = -K_N * q_p$, where $q_p$ represents the joint angular velocity of one or more joints of robotic arm 204 and $K_N$ represents the neural monitor gain. Joint angular velocity $q_p$ may be measured, e.g., by one or more sensors at robotic arm 204. Neural monitor gain $K_N$ may be variable based on the distance between surgical tool 210 and a portion of the patient's anatomy, such as spinal cord 103, as measured by neural monitor 280, for example. In one embodiment, $K_N$ may be represented as a piecewise function such as:

$$K_N = \begin{cases} K_D & \Delta x_n < 0 \\ K_D(x_s - \Delta x_n)/x_S & 0 < \Delta x_n < x_s \\ 0 & \Delta x_n > x_s \end{cases} \quad (2)$$

where $K_D$ is a maximum damping gain, $x_s$ is a predetermined minimum safe distance, and $\Delta x_n$ is the distance between distal end 211 of surgical tool 210 and spinal cord 103 measured by neural monitor 280. $K_D$ may be a predetermined constant value that may be selected to optimize the performance of CAS system 200. Safe distance $x_s$ may be determined based on, e.g., input from the surgeon. In certain embodiments, safe distance $x_s$ may be determined based on the accuracy of neural monitor 280. For example, if neural monitor 280 is capable of accurately determining a distance between distal end 211 and spinal cord 103 within y millimeters, then $x_s$ may be determined to be a value equal to (3*y) millimeters.

In another embodiment, $K_N$ may be defined in accordance with the following equation:

$$K_N = \begin{cases} K_D & \Delta x_n < 0 \\ K_D(x_s - \Delta x_n)/x_S & x_f < \Delta x_n < x_s \\ 0 & \Delta x_n > x_s \end{cases} \quad (3)$$

In equation (3), a threshold $x_f$ is defined such that $K_N$ is equal to the maximum damping gain $K_D$ when the distance $\Delta x_n$ less than $x_f$. Thus, in equation (3), the maximum damping gain may be applied when distal end 211 is less than a predetermined distance $x_f$ away from spinal cord 103, resulting in an increased impedance at distances where $\Delta x_n$ is still greater than 0. Threshold $x_f$ may likewise be determined based on, e.g., input from the surgeon or other user and/or based on the accuracy of neural monitor 280.

Equations (2) and (3) are merely exemplary equations for determining the value of $K_N$. In fact, $K_N$ may be expressed by any other equation such that $K_N$ increases as $\Delta x_n$ decreases over a particular range. For example, any number of linear and/or nonlinear functions may be used to represent an increase in impedance proportional to a decrease in distance between distal end 211 of surgical tool 210 and spinal cord 103. Moreover, while the embodiment discussed above calculates a virtual damping torque, those skilled in the art will appreciate that any combination of stiffness, inertia, and/or damping forces and torques may be introduced to CAS system 200 based on the distance between surgical tool 210 and spinal cord 103, as measured by neural monitor 280.

In exemplary embodiments of FIG. 5, torque $\tau_d$, generated based on the virtual haptic geometry, may be combined with a neural monitor torque $\tau_n$ generated based on a distance between surgical tool 210 and a portion of the patient's anatomy, measured by, e.g., neural monitor 280. For example, returning to FIG. 5, processor 231 may add together $\tau_n$ and $\tau_d$ to produce $\tau_c$ (block 540), a total torque value to be provided as a haptic feedback command to the force system of robotic arm 204 (block 550). Block 550 in FIG. 5 may represent the robotic dynamics of the physical system of robotic arm 204. Thus, the haptic feedback command $\tau_c$ may be provided to robotic arm 204, and one or more sensors at robotic arm 204 or elsewhere may feed back information regarding the orientation and movement of robotic arm 204. For example, as shown in FIG. 5, the joint angular velocity $q_p$ of robotic arm 204 and the actual position x of surgical tool 210 may be fed back to blocks 560 and 510, respectively.

Figure 6:
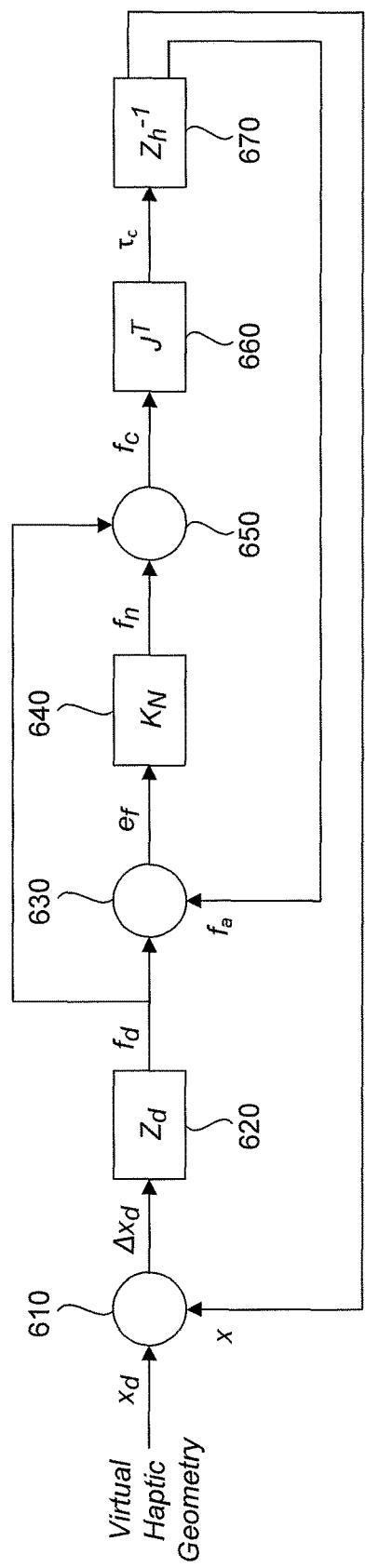
FIG. 6 is another block diagram of another exemplary control system which may be employed by the CAS system illustrated in FIG. 2.

FIG. 6 shows a system control diagram in accordance with another exemplary embodiment. In FIG. 6, processor 231 may control robotic arm 204 by means of impedance control with force feedback. That is, processor 231 may generate a dynamic impedance in robotic arm 204 by altering a contribution of a force feedback gain being applied to robotic arm 204. For example, processor 231 may alter the contribution of force feedback gain based on the distance between surgical tool 210 and spinal cord 103, as measured by neural monitor 280. The system control diagram of FIG. 6 may be used, for example, in combination with a robotic arm that exhibits high natural stiffness, damping, and/or inertia and thus may be difficult to move in its natural state. This natural impedance may be based, for example, on a transmission in robotic arm 204 having a high gear ratio. Thus, in the embodiment of FIG. 6, processor 231 may reduce an amount of force feedback gain being applied to robotic arm 204 as distal end 211 moves closer to spinal cord 103 so that the impedance of robotic arm 204 increases as distal end 211 moves closer to spinal cord 103.

For example, in FIG. 6, processor 231 may receive a desired position $x_d$ and an actual position x of surgical tool 210, similar to the embodiment of FIG. 5. Processor 231 may also calculate a difference $\Delta x_d$ between the desired position and the actual position of surgical tool 210 (block 610), and may then calculate a haptic object force $f_d$ based on difference $\Delta x_d$ (block 620). For example, processor 231 may calculate $f_d$ by multiplying difference $\Delta x_d$ by a haptic object impedance value $Z_d$. In certain embodiments, haptic object impedance value $Z_d$ may be a fixed value for the haptic object to which it corresponds. For example, haptic object impedance value $Z_d$ may be 3,000 N/m for a particular haptic object. In other embodiments, discussed in greater detail below, haptic object impedance value $Z_d$ may be variable.

Moreover, in one embodiment, haptic object impedance value $Z_d$ may include several components, such as an inertia component M, a damping component B, and a stiffness component K. In this embodiment, processor 231 may also determine a first derivative and/or a second derivative of the difference values $\Delta x_d$, and may calculate haptic object force $f_d$ based on the impedance components M, B, and/or K as well as $\Delta x_d$ and its first and/or second derivatives. For example, processor 231 may determine $f_d$ in accordance with equation (1), discussed above. In one embodiment, M may be equal to zero, such that $f_d$ is determined based on a damping component B and a stiffness component K.

Processor 231 may determine a difference between haptic object force $f_d$ and applied force $f_a$ to determine a force error value $e_f$ (block 630). Applied force $f_a$ may represent an amount of force being applied to robotic arm 204 by a user (e.g., a surgeon). For example, as discussed above with regard to FIG. 3, robotic arm 204 may include one or more force sensors 270 to measure an amount of force being applied to it by the user. Robotic arm 204 may then send electronic signals indicative of the applied force values $f_a$ to processor 231.

Processor 231 may then generate a modified force feedback value $f_n$ such that $f_n = e_f * K_N$, where $K_N$ represents the neural monitor gain (block 640). Neural monitor gain $K_N$ may be variable based on the distance between surgical tool 210 and a portion of the patient's anatomy, such as spinal cord 103, as measured by neural monitor 280, for example. For example, in one embodiment, $K_N$ may be represented as a piecewise function such as:

$$K_N = \begin{cases} 0 & \Delta x_n < 0 \\ (K_F \Delta x_n)/x_S & 0 < \Delta x_n < x_s, \\ K_F & \Delta x_n > x_s \end{cases} \quad (4)$$

where $K_F$ is a maximum force feedback gain, $x_s$ is a predetermined minimum safe distance, and $\Delta x_n$ is the distance between distal end 211 of surgical tool 210 and spinal cord 103. $K_F$ may be a predetermined constant value that may be selected to optimize the performance of CAS system 200. Safe distance $x_s$ may be determined based on, e.g., input from the surgeon. In certain embodiments, $x_s$ may be determined based on the accuracy of neural monitor 280. For example, if neural monitor 280 can accurately determine a distance between distal end 211 and spinal cord 103 within y millimeters, then $x_s$ may be determined to be a value equal to (3*y) millimeters.

Equation (3) is an exemplary equation for determining the value of $K_N$. In fact, $K_N$ may be expressed by any other equation such that $K_N$ decreases as $\Delta x_n$ decreases over a particular range for embodiments associated with FIG. 6. By decreasing the neural monitor gain $K_N$ for a corresponding decrease in the distance $\Delta x_n$ between distal end 211 and spinal cord 103, processor 231 may reduce the force feedback of robotic arm 204 to zero (or a near-zero value) based on the proximity of surgical tool 210 to the nervous system. If, as discussed above, robotic arm 204 exhibits high natural impedance, then reducing the force feedback will make robotic arm 204 (e.g., articulated arm 206) increasingly difficult to move as distal end 211 moves closer to spinal cord 103.

Moreover, any number of linear and/or nonlinear functions may represent $K_N$ so as to generate an increased impedance proportional to a decrease in distance spinal cord 103. Moreover, in another embodiment, equation (4) may be modified to include a threshold $x_f$ defined such that the force feedback gain is zero when the distance between distal end 211 and spinal cord 103 is within the threshold distance $x_f$. For example, $K_N$ may be represented as:

$$K_N = \begin{cases} 0 & \Delta x_n < x_f \\ K_F(\Delta x_n - x_f)/(x_s - x_f) & 0 < \Delta x_n < x_s. \\ K_F & \Delta x_n > x_s \end{cases} \quad (5)$$

Still further, equation (5) may be modified to be a non-linear function of the distance between distal end 211 and spinal cord 103 such that:

$$K_N = \begin{cases} 0 & \Delta x_n < x_f \\ K_F(\Delta x_n - x_f)/(x_s - x_f) & 0 < \Delta x_n < x_s, \\ K_F & \Delta x_n > x_s \end{cases} \quad (6)$$

where b is a scalar coefficient greater than 1. Those skilled in the art will appreciate that other equations may be used to represent $K_N$, consistent with the spirit and scope of the disclosed embodiments.

After calculating the modified force feedback value $f_n$, as described above, processor 231 may generate a combined force value $f_c$ by adding a feedforward value of $f_d$ and the modified force feedback value $f_n$ (block 650). Processor 231 may then utilize the Jacobian transpose to determine a haptic feedback command $\tau_c$ with a torque value corresponding to the combined force value $f_c$ (block 660).

Processor 231 may provide haptic feedback command $\tau_c$ to the force system of robotic arm 204 (block 670). For example, block 670 in FIG. 6 may represent the robotic dynamics of the physical system of robotic arm 204. Thus, the haptic feedback command $\tau_c$ may be provided to robotic arm 204, and one or more sensors at robotic arm 204 or elsewhere may feed back information regarding the orientation and movement of robotic arm 204, as well as forces being applied thereto. For example, as shown in FIG. 6, the actual position x of surgical tool 210 may be fed back to block 610 and, as discussed above, a force $f_a$ being applied by the surgeon to robotic arm 204 may be fed back to block 630.

Figure 7:
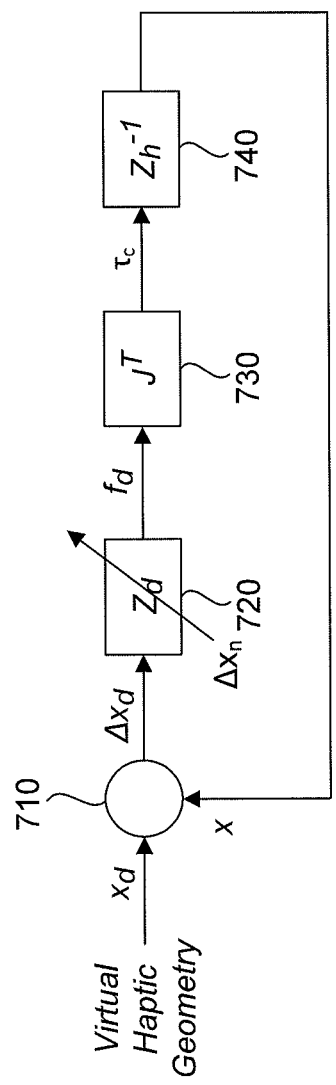
FIG. 7 is another block diagram of yet another exemplary control system which may be employed by the CAS system illustrated in FIG. 2.

FIG. 7 shows a system control diagram in accordance with yet another exemplary embodiment. In FIG. 7, processor 231 may control robotic arm 204 by direct modification of haptic object impedance value $Z_d$. For example, as discussed above with regard to FIGS. 5 and 6, haptic object impedance value $Z_d$ may be a fixed value for the haptic object to which it corresponds. However, in FIG. 7, processor 231 may dynamically alter haptic object impedance value $Z_d$ based on, e.g., the distance between distal end 211 of surgical tool 210 and a portion of the patient's anatomy, such as spinal cord 103, as measured by neural monitor 280.

For example, in FIG. 7, processor 231 may receive a desired position $x_d$ and an actual position x of surgical tool 210, as discussed above with respect to FIG. 5. Processor 231 may also calculate a difference $\Delta x_d$ between the desired position and the actual position of surgical tool 210 (block 710), and may then calculate a force, $f_d$, based on difference $\Delta x_d$ (block 720). For example, processor 231 may calculate $f_d$ in accordance with equation (1), discussed above. However, in embodiments associated with FIG. 7, one or more of an inertia component M, a damping component B, and a stiffness component K of impedance value $Z_d$, as shown in equation (1), may be variable functions of $\Delta x_n$. In certain embodiments, one or more of M, B, or K may be defined as a piecewise linear or non-linear function of $\Delta x_n$. For example, damping component B may be defined as:

$$B = \begin{cases} B_{max} & \Delta x_n < x_f \\ B_{max}(\Delta x_n - x_s)/(x_f - x_s) & x_f < \Delta x_n < x_s, \\ 0 & \Delta x_n > x_s \end{cases} \quad (7)$$

where $B_{max}$ is a maximum damping component value, $x_s$ is a predetermined minimum safe distance, $x_f$ is a threshold value, and $\Delta x_n$ is the distance between distal end 211 of surgical tool 210 and spinal cord 103. $B_{max}$ may be a predetermined constant value that may be selected to optimize the performance of CAS system 200. Safe distance $x_s$ and threshold $x_f$ may be determined based on, e.g., input from the surgeon or other user or based on the accuracy of neural monitor 280. While equation (7) defines B as having a value of 0 for $\Delta x_n > x_s$, B may also be defined to be some non-zero value $B_{min}$ for this range. For example, $B_{min}$ may represent a minimum damping present in robotic arm 204 and may be selected in a manner that optimizes the performance of CAS system 200. Moreover, equation (7) is merely an exemplary equation for representing B, and those skilled in the art will appreciate that B may be represented by other equations, such as a non-linear piecewise equation or any other linear or non-linear equations consistent with disclosed embodiments. Also, while stiffness component B is used in the example above, inertia component M and stiffness component K may also be represented by equations similar to those described above with respect to damping component B. By varying one or more of M, B, or K as a function of $\Delta x_n$, processor 231 may calculate a variable haptic object impedance value $Z_d$ such that $Z_d$ also varies based on $\Delta x_n$,
the distance between surgical tool 210 and a portion of the patient's anatomy, such as spinal cord 103, as measured by neural monitor 280.

After calculating force $f_d$, processor 231 may calculate a torque to be applied to robotic arm 204 as haptic feedback command $\tau_c$ (block 730). Thus, at block 730, processor 231 may utilize the Jacobian transpose to determine a torque $\tau_c$ with a value corresponding to the desired force value $f_d$.

Processor 231 may then provide haptic feedback command $\tau_c$ to the force system of robotic arm 204 to control one or more actuators at corresponding joints of robotic arm 204 (block 740). For example, block 740 of FIG. 7 may represent the robotic dynamics of the physical system of robotic arm 204. Thus, haptic feedback command $\tau_c$ may be provided to robotic arm 204, and one or more sensors at robotic aim 204 or elsewhere may feed back information regarding the orientation and movement of robotic arm 204. For example, as shown in FIG. 7, the actual position x of surgical tool 210 may be fed back to block 710.

Figure 8:
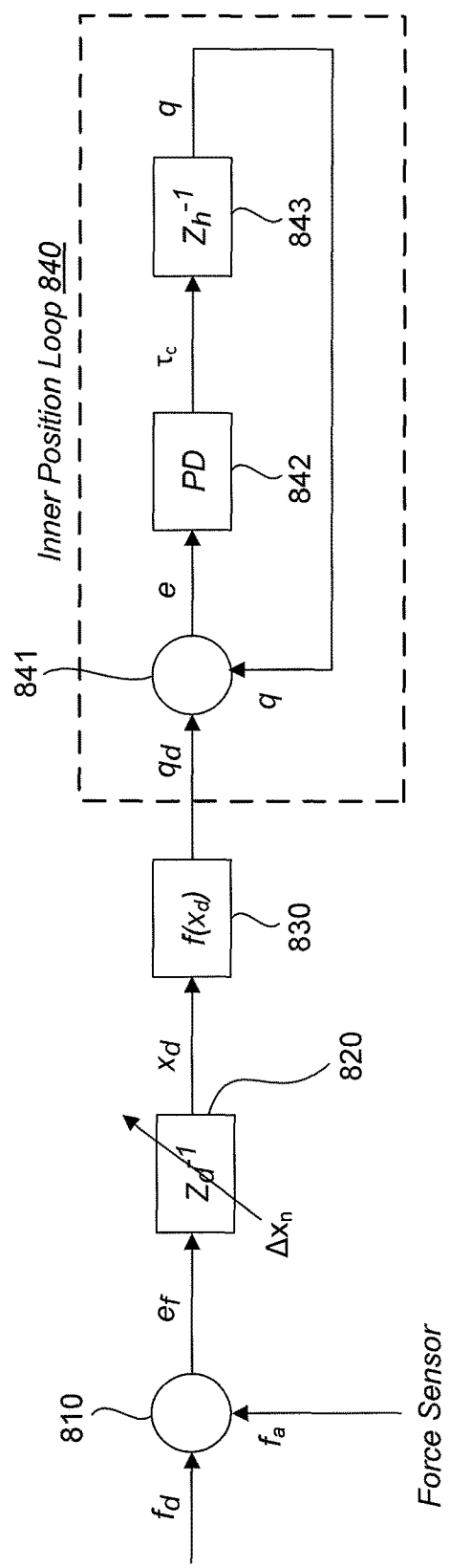
FIG. 8 is another block diagram of yet another exemplary control system which may be employed by the CAS system illustrated in FIG. 2.

FIG. 8 shows a system control diagram in accordance with yet another exemplary embodiment. In FIG. 8, processor 231 may control robotic arm 204 by direct modification of a haptic object admittance value $Z_d^{-1}$. For example, the control system illustrated in FIG. 8 may be an admittance-based control system, such that processor 231 receives measurements of forces being applied to robotic arm 204, generates a desired position of robotic arm 204 based on the measured forces, and then sends commands to drive robotic arm 204 to the desired position.

For example, in FIG. 8 processor 231 may receive a desired force value $f_d$ and an applied force value $f_a$. Desired force value $f_d$ represents the desired force at an end effector of robotic arm 204 (e.g., surgical tool 210) and may be a constant value or may be variable. In one embodiment, robotic arm 204, at times, may be operated in a zero-gravity mode where $f_d$=0. Applied force $f_a$ represents a force being applied to surgical tool 210 by a user, e.g., a surgeon. For example, as discussed above, CAS system 200 may include one or more force sensors 270 for measuring applied force $f_a$. Force sensors 270 may send a signal to processor 231 indicative of applied force $f_a$. Processor 231 may determine a force error value $e_f$ such that $e_f=f_d-f_a$ (block 810).

Processor 231 may determine a desired position $x_d$ of surgical tool 210 based on the determined force error value $e_f$ (block 820). Desired position $x_d$ may include a point or set of points in three-dimensional space that represent the desired position of surgical tool 210. Processor 231 may determine desired position $x_d$ based on a haptic object admittance $Z_d^{-1}$. Haptic object admittance value $Z_d^{-1}$ may be defined such that $x_d$ may be determined in accordance with the following equation:

$$e_f = M(\ddot{x}_d) + B(\dot{x}_d) + K(x_d). \quad (8)$$

where M, B, and K are inertia, damping, and stiffness components, respectively. In embodiments associated with FIG. 8, one or more of M, B, and K may be variable functions of $\Delta x_n$, such that the haptic object admittance $Z_d^{-1}$ is also variable based on $\Delta x_n$, the distance between distal end 211 of surgical tool 210 and spinal cord 103, as measured by neural monitor 103. In certain embodiments, one or more of M, B, or K may be defined as a piecewise linear or non-linear function of $\Delta x_n$. For example, M, B, and/or K may be defined as discussed above with respect to FIG. 7. Processor 231 may then solve equation (8) to determine desired position $x_d$ for a given force error $e_f$ using, e.g., numerical integration.

Processor 231 may use desired position $x_d$ to determine one or more desired joint angular positions $q_d$ for the corresponding one or more joints of robotic arm 204 (block 830). For example, processor 231 may use one or more coordinate transform functions and/or inverse kinematics functions, $f(x_d)$, to translate the desired position $x_d$ in three-dimensional space to one or more joint angular positions $q_d$, e.g., in angular space, that result in surgical tool 210 being positioned in desired position $x_d$.

Processor 231 may send commands to one or more actuators in robotic arm 204 such that the actual joint angular positions q of robotic arm 204 (e.g., of articulated arm 206) equal their corresponding desired joint angular positions $q_d$. Processor 231 may generate these commands using a feedback control loop such as inner position loop 840. For example, processor 231 may compare desired joint angular positions $q_d$ to actual joint angular positions q to determine a joint angular position error $e=q_d-q$ (block 841). Actual joint angular positions q may be measured by one or more sensors at robotic arm 204.

Processor 231 may determine a torque value for a haptic feedback command $\tau_c$ using, e.g., a proportional plus derivative controller (block 842). Processor 231 may then provide haptic feedback command $\tau_c$ to the force system of robotic arm 204 to control one or more actuators at corresponding joints of robotic arm 204 (block 843). For example, block 843 of FIG. 7 may represent the robotic dynamics of the physical system of robotic arm 204. Thus, processor 231 may provide haptic feedback command $\tau_c$ to robotic arm 204, and one or more sensors at robotic arm 204 or elsewhere may feed back information regarding the orientation and movement of robotic arm 204. For example, as shown in FIG. 8, the actual joint angular positions q of robotic arm 204 may be fed back to block 710.

Figure 9:
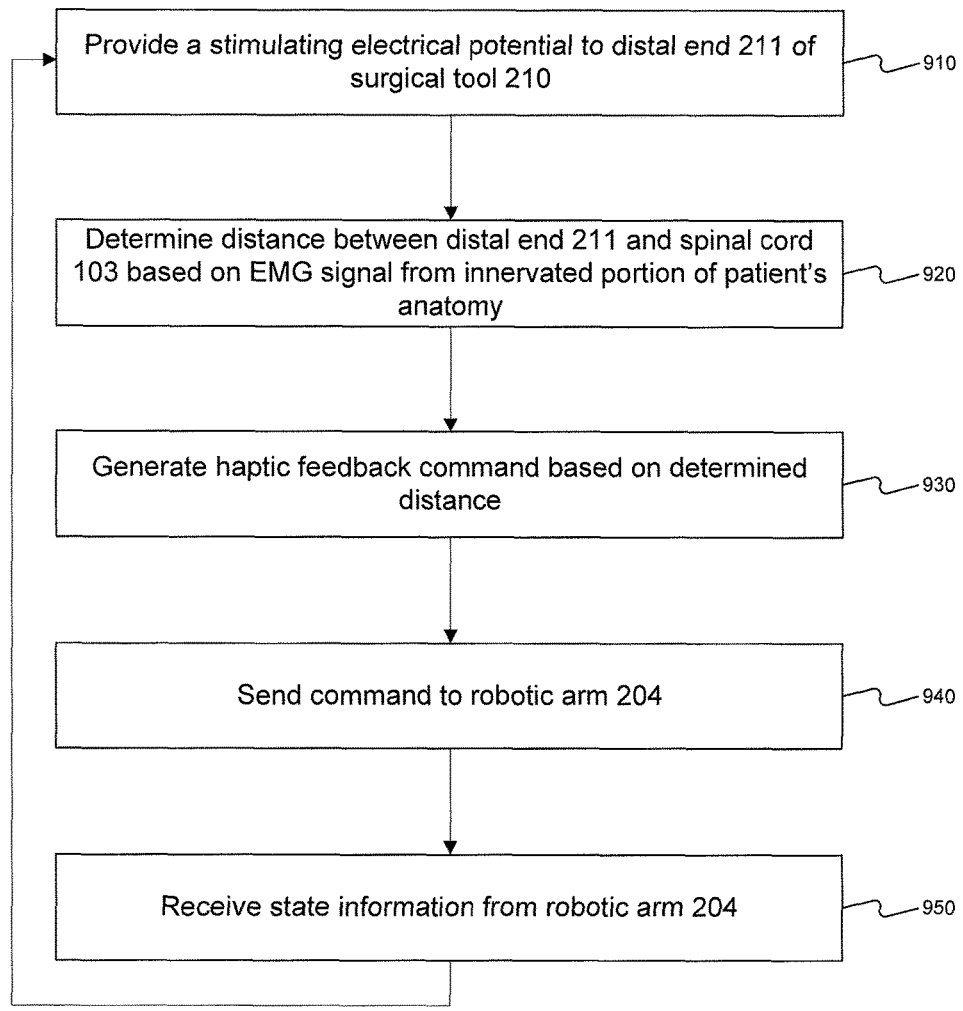
FIG. 9 is a flowchart of an exemplary method for dynamically generating haptic feedback commands consistent with disclosed embodiments.

FIG. 9 illustrates a flowchart of an exemplary neural monitor-based dynamic haptics process that may be performed by, e.g., CAS system 200 or one or more of its components. According to the exemplary process of FIG. 9, CAS system 200 may provide a stimulating electrical potential to distal end 211 of surgical tool 210 (step 910). The stimulating potential may be generated, e.g., by neural monitor 280, as discussed above.

CAS system 200 may also determine a distance between distal end 211 and spinal cord 103 based on an EMG signal received from an innervated portion of the patient's anatomy (step 920). For example, the stimulating potential applied in step 910 may cause nerves in spinal cord 103 to innervate one or more muscles or other groups of tissue near or around spinal cord 103. One or more sensors associated with neural monitor 280 may detect EMG signals generated by the muscles or other tissue innervated by spinal cord 103. Based on an intensity of the EMG signal received, neural monitor 280 may determine a distance between distal end 211 and spinal cord 103.

Based on the determined distance, CAS system 200 may generate haptic feedback commands used to control robotic arm 204 (step 930). That is, CAS system 200 may dynamically alter the haptic feedback commands being sent to robotic arm 204 based on a determined distance between distal end 211 and spinal cord 103. For example, CAS system 200 may dynamically vary the degree to which robotic arm 204 resists movement based on the signals received from neural monitor 280, e.g., according to one or more of the embodiments discussed above with regard to FIGS. 5-8.

Once the command is generated, CAS system 200 may send the command to robotic arm 204 (step 940). For example, CAS system 200 may send the command via an I/O device to the force system or the control system of robotic arm 204. Robotic arm 204 may then send corresponding commands to one or more actuators in robotic arm 204 to control movement and/or forces within robotic arm 204 based on the received haptic feedback command.

CAS system 200 may also receive state information from robotic arm 204 (step 950). For example, as discussed above, robotic arm 204 may include one or more sensors, such as applied force sensors, joint angular position sensors, joint angular velocity sensors, or any other sensors, to determine a state of robotic arm 204. Signals from one or more of these sensors may be fed back to CAS system 200. For example, in embodiments discussed above with respect to FIG. 5, position signal x and joint angular velocity signal $q_p$ are fed back to CAS system 200.

CAS system 200 may continuously repeat steps 910-950 such that CAS system 200 continuously monitors a distance between distal end 211 of surgical tool 210 and spinal cord 103, and dynamically generates and sends haptic feedback commands to robotic arm 204 based on the determined distance.

The presently disclosed systems and methods provide a solution that enables a computer-assisted surgical system to dynamically alter a degree to which a robotic arm of the system resists movement based on a distance between a surgical tool of the robotic arm and a portion of the patient's anatomy, such as a spinal cord, detected by a neural monitor. By dynamically altering the degree to which the robotic arm resists movement, systems and method consistent with disclosed embodiments may provide haptic feedback to a surgeon operating the robotic aim based on a measured proximity to the spinal cord or other nerves. As a result, the disclosed systems and methods may prevent a surgeon from unwanted interaction with or damage to the patient's spinal cord or other nerves.

Moreover, as discussed above, systems and methods consistent with the disclosed embodiments may dynamically alter a degree to which the robotic arm resists movement in several different ways. For example, exemplary systems and methods may alter the degree to which a robotic arm resists movement by generating a damping torque based on the distance measured by the neural monitor. Further, such systems and methods may alter the degree to which a robotic arm resists movement by modifying an amount of force feedback being applied to the robotic arm based on the measured distance. Still further, such systems and methods may alter the degree to which a robotic arm resists movement by directly modifying a haptic object impedance or haptic object admittance value based on the measured distance.

It will be apparent to those skilled in the art that various modifications and variations can be made to the disclosed systems and associated methods for neural monitor-based dynamic haptics. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A computer-implemented method for controlling a surgical system, the method comprising:
   receiving, from a neural monitor, a signal indicative of a distance between a surgical tool connected to a robotic device and a portion of a patient's anatomy;

receiving a joint angular velocity of one or more joints of the robotic device;

determining a neural monitor gain based on the signal received from the neural monitor;

generating a first force value based on the neural monitor gain and the joint angular velocity of the one or more joints of the robotic device;

generating a second force value based on a relationship of a surgical tool and a virtual boundary associated with the patient's anatomy; and generating a robotic control to control the surgical system by altering movement of the robotic device based upon the first force value and the second force value.

2. The computer-implemented method of claim 1, wherein the virtual boundary defines a volume associated with a sensitive portion of the patient's anatomy.

3. The computer-implemented method of claim 2, wherein the virtual boundary is configured to generate feedback forces that prevent movement of the surgical tool from crossing the virtual boundary associated with the sensitive portion of the patient's anatomy.

4. The computer-implemented method of claim 1, wherein generating the first force value further comprises:

subtracting an applied force being applied to a robotic arm of the robotic device from the second force value to calculate a force error and generating the first force value proportional to the force error and the neural monitor gain.

5. The computer-implemented method of claim 1, the method further comprising:

providing an electrical potential to the surgical tool;

measuring an electromyographic signal at another portion of the patient's anatomy innervated by the portion of the patient's anatomy; and generating the signal indicative of the distance between the surgical tool and the portion of the patient's anatomy based on the electromyographic signal.

6. A computer-assisted surgery system comprising:

a robotic device including a surgical tool;

a processor communicatively connected to the robotic device and configured to:

receive, from a neural monitor, a signal indicative of a distance between the surgical tool and a portion of a patient's anatomy;

receive a joint angular velocity of one or more joints of the robotic device;

determine a neural monitor gain based on the signal received from the neural monitor;

generate a first force value based on the neural monitor gain and the joint angular velocity of the one or more joints of the robotic device;

generate a second force value based on a relationship of a surgical tool and a virtual boundary associated with the patient's anatomy; and generate a robotic control to control the surgical system by altering movement of the robotic device based upon the first force value and the second force value.

7. The computer-assisted surgery system of claim 6, further comprising the neural monitor, wherein the neural monitor is configured to:

provide an electrical potential to the surgical tool;

measure an electromyographic signal at another portion of the patient's anatomy innervated by the portion of the patient's anatomy; and generate the signal indicative of the distance between the surgical tool and the portion of the patient's anatomy based on the electromyographic signal.

* * * * *